United States Patent [19]

Gehring et al.

[11] Patent Number: 4,787,930

[45] Date of Patent: Nov. 29, 1988

[54] 5-AMINO-1-PHENYL-PYRAZOLE HERBICIDES AND PLANT GROWTH REGULATORS

[75] Inventors: Reinhold Gehring, Wuppertal; Otto Schallner, Monheim; Jörg Stetter, Wuppertal; Hans-Joachim Santel, Leverkusen; Robert R. Schmidt; Klaus Lürssen, both of Bergisch Gladbach, all of Fed. Rep. of Germany

[73] Assignee: Bayer Aktiengesellschaft, Leverkusen, Fed. Rep. of Germany

[21] Appl. No.: 4,353

[22] Filed: Jan. 16, 1987

[30] Foreign Application Priority Data

Feb. 4, 1986 [DE] Fed. Rep. of Germany ....... 3603291

[51] Int. Cl.$^4$ .................... A01N 43/56; C07D 231/38
[52] U.S. Cl. ........................................ 71/92; 548/101; 548/362; 548/375; 548/376; 548/377
[58] Field of Search ............... 548/101, 362, 375, 376, 548/377; 71/92

[56] References Cited

U.S. PATENT DOCUMENTS 4,614,533  9/1986  Schallner et al. ...................... 71/92

FOREIGN PATENT DOCUMENTS 0138149  4/1985  European Pat. Off. ............ 548/362
0154115  9/1985  European Pat. Off. ............ 548/367
3423582  1/1986  Fed. Rep. of Germany ...... 548/362

Primary Examiner—Mary C. Lee
Assistant Examiner—Kurt G. Briscoe
Attorney, Agent, or Firm—Sprung Horn Kramer & Woods

[57] ABSTRACT

Herbicidal and plant growth regulating 5-amino-1-phenyl-pyrazoles of the formula

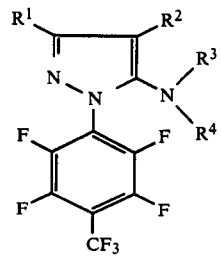

in which $R^1$ to $R^4$ each represents hydrogen or various organic radicals, X represents oxygen or sulphur, n represents the number 0, 1 or 2, and m represents the number 1, 2 or 3, but wherein, in the case where $R^1$ and $R^3$ represent hydrogen and $R^2$ represents nitro, $R^4$ does not simultaneously represent a propionyl radical.

15 Claims, No Drawings

5-AMINO-1-PHENYL-PYRAZOLE HERBICIDES AND PLANT GROWTH REGULATORS

The invention relates to new 5-amino-1-phenyl-pyrazoles, several processes for their preparation and their use as herbicides and plant growth regulators.

It is known that certain 5-amino-1-phenyl-pyrazoles, such as, for example, 4-nitro-5-propionamido-1-(2,3,5,6-tetrafluoro-4-trifluoromethyl-phenyl)-pyrazole, have herbicidal properties, and in particular also selective herbicidal properties (compare, for example, DE-OS (German Published Specification) No. 3,402,308).

Their herbicidal action against hermful plants, however, like their tolerance towards important crop plants, is not always completely satisfactory in all fields of use.

New 5-amino-1-phenyl-pyrazoles of the general formula (I)

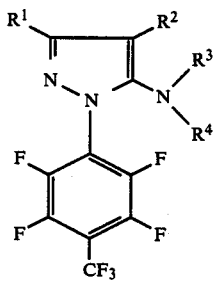

in which
R$^1$ represents hydrogen, or represents alkyl with 1 to 12 carbon atoms,
R$^2$ represents hydrogen, nitro, nitroso or halogen, or represents a radical

wherein
R$^5$ represents hydrogen, hydroxyl, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
R$^3$ represents hydrogen, or represents a radical

or represents a radical —S(O)$_n$—R$^7$ and R$^4$ represents hydrogen, or represents alkyl, or represents a radical

or represents a radical —S(O)$_n$—R$^7$, or, in the case where R$^3$ represents a —SO$_2$—R$^7$ radical or a —CO—C$_m$F$_{2m+1}$ radical, also represents an inorganic or organic cation bonded in salt form,
wherein
R$^6$ represents hydrogen, alkyl, alkenyl, alkinyl, halogenoalkyl, alkoxyalkyl, alkylthioalkyl, alkylsulphonylalkyl or alkylsulphinylalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
X represents oxygen or sulphur,
n represents the number 0, 1 or 2,
m represents the number 1, 2 or 3 and
R$^7$ represents alkyl or halogenoalkyl, or represents optionally substituted aryl,
but wherein, in the case where R$^1$ and R$^3$ represent hydrogen and R$^2$ represents nitro, R$^4$ does not simultaneously represent a propionyl radical, have been found.

It has furthermore been found that the new 5-amino-1-phenyl-pyrazoles of the general formula (I)

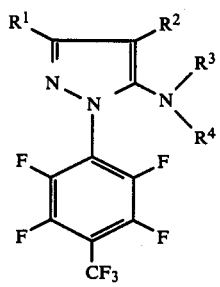

in which
R$^1$ represents hydrogen, or represents alkyl with 1 to 12 carbon atoms,
R$^2$ represents hydrogen, nitro, nitroso or halogen, or represents a radical

wherein
R$^5$ represents hydrogen, hydroxyl, alkyl, alkenyl, alkinyl, halogenoalkyl, alkoxyalkyl or alkylthioalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino,
R$^3$ represents hydrogen, or represents a radical

or represents a radical —S(O)$_n$—R$^7$ and
R$^4$ represents hydrogen, or represents alkyl, or represents a radical

or represents a radical —S(O)$_n$—R$^7$, or, in the case where R$^3$ represents a —SO$_2$—R$^7$ radical or a —CO—C$_m$F$_{2m+1}$ radical, also represents an inorganic or organic cation bonded in salt form, R$^6$ represents hydrogen, alkyl, alkenyl, alkinyl, halogenoalkyl, alkoxyalkyl, alkylthioalkyl, alkylsulphonylalkyl or alkylsulphinylalkyl, or represents optionally substituted cycloalkyl, or represents optionally substituted aryl, or represents alkoxy or alkylthio, or represents optionally substituted aryloxy, or represents optionally substituted arylthio, or represents alkylamino or dialkylamino, or represents optionally substituted arylamino, X represents oxygen or sulphur, n represents the number 0, 1 or 2, m represents the number 1, 2 or 3 and R$^7$ represents alkyl or halogenoalkyl, or represents optionally substituted aryl, but wherein, in the case where R$^1$ and R$^3$ represent hydrogen and R$^2$ represents nitro, R$^4$ does not simultaneously represent a propionyl radical, can be prepared by the following processes:

(a) the 5-amino-1-phenyl-pyrazole derivatives according to the invention, of the formula (Ia)

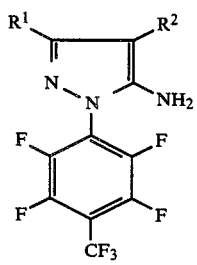

in which

R$^1$ and R$^2$ have the abovementioned meaning, are obtained by a process in which 2,3,5,6-tetrafluoro-4-trifluoromethyl-phenylhydrazine of the formula (II)

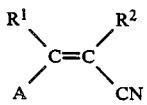

is first reacted with acrylonitrile derivatives of the formula (III)

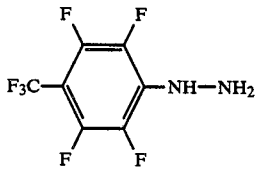

in which

R$^1$ and R$^2$ have the abovementioned meaning and

A represents halogen, hydroxyl, alkoxy or dialkylamino, in a 1st stage, if appropriate in the presence of a diluent and if appropriate in the presence of a reaction auxiliary, to give the phenylhydrazine derivatives of the formula (IV)

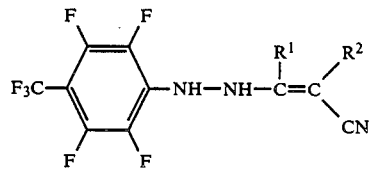

in which

R$^1$ and R$^2$ have the abovementioned meaning, and these are cyclized in a 2nd stage, if appropriate in the presence of a diluent and if appropriate in the presence of an acid-binding agent, or (b) the 5-amino-1-phenyl-pyrazole derivatives according to the invention, of the formula (Ib)

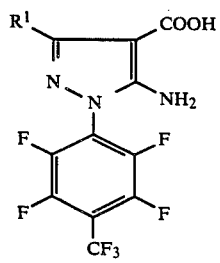

in which

R$^1$ has the abovementioned meaning, are obtained by a process in which 4-alkoxycarbonyl-5-amino-pyrazoles of the formula (Ir)

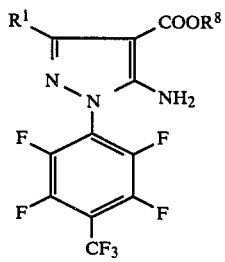

in which

R$^1$ has the abovementioned meaning and

R$^8$ represents alkyl, are hydrolyzed on the ester group in the 4-position of the pyrazole ring in the generally customary manner, if appropriate in the presence of a diluent and if appropriate in the presence of a catalyst, or (c) the 5-amino-1-phenyl-pyrazole derivatives according to the invention, of the formula (Ic)

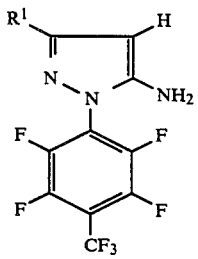

in which

R¹ has the abovementioned meaning,
are obtained by a process in which 5-amino-1-phenyl-pyrazole derivatives of the formula (Ib)

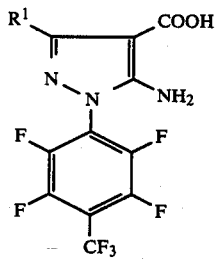 (Ib)

in which

R¹ has the abovementioned meaning,
are decarboxylated in the generally customary manner, if appropriate in the presence of a diluent and if appropriate in the presence of a catalyst, or (d) the 5-amino-1-phenyl-pyrazole derivatives according to the invention, of the formula (Id)

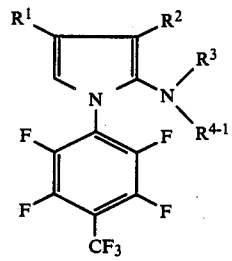 (Id)

in which $R^{4-1}$ represents alkyl, or represents a radical

, or represents a radical $-S(O)_n-R^7$ and
$R^1$, $R^2$, $R^3$, $R^6$, $R^7$, X and n have the above-mentioned meaning,
are obtained by a process in which 5-amino-1-phenyl-pyrazoles of the formula (Is)

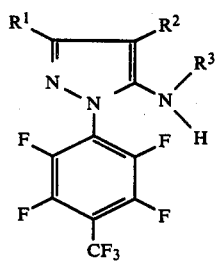 (Is)

in which $R^1$, $R^2$ and $R^3$ have the abovementioned meaning,
are reacted (d-α) with compounds of the formula (V)

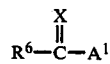 (V)

in which

A¹ represents halogen, or represents a radical

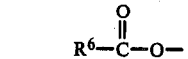

and

R⁶ and X have the abovementioned meaning,
or (d-β) with compounds of the formula (Va)

 (Va)

in which

A² represents halogen and
R⁷ and n have the abovementioned meaning,
or (d-γ) with compounds of the formula (Vb)

 (Vb)

in which $R^{8-1}$ represents alkyl and
A³ represents halogen, p-toluenesulphonyloxy or alkoxysulphonyloxy,
if appropriate in the presence of a diluent and if appropriate in the presence of an acid-binding agent, or (e) the 5-amino-1-phenyl-pyrazole derivatives according to the invention, of the formula (Ie)

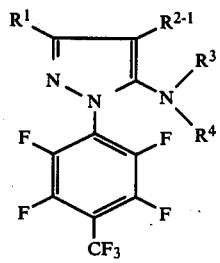 (Ie)

in which $R^{2-1}$ represents halogen, nitro, nitroso, formyl, alkanoyl or aroyl and
$R^1$, $R^3$ and $R^4$ have the abovementioned meaning,
are obtained by a process in which 5-amino-1-phenyl-pyrazole derivatives of the formula (It)

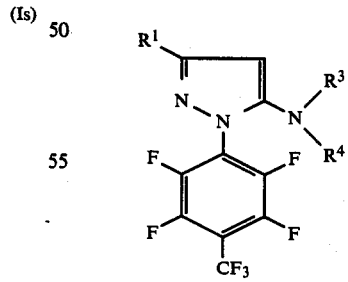 (It)

in which $R^1$, $R^3$ and $R^4$ have the abovementioned meaning,
are subjected to substitution in the 4-position with electrophilic agents of the formula (VI)

 (VI)

in which $A^4$ represents an electron-withdrawing leaving group and $R^{2-1}$ has the abovementioned meaning, or with other customary electrophilic agents, if appropriate in the presence of a diluent and if appropriate in the presence of a catalyst or reaction auxiliary, or (f) the 5-amino-1-phenyl-pyrazole derivatives according to the invention, of the formula (If)

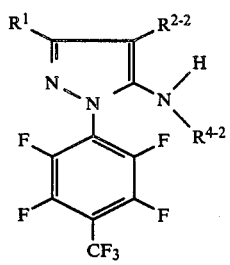
(If)

in which $R^{2-2}$ represents halogen, nitro or nitroso, $R^{4-2}$ represents hydrogen or alkyl and $R^1$ has the abovementioned meaning, are obtained by a process in which 5-acylamino-1-phenylpyrazoles of the formula (Iμ)

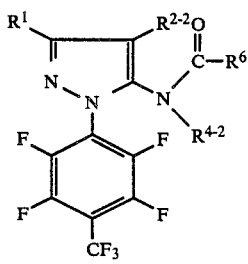
(Iu)

in which $R^1$, $R^{2-2}$, $R^{4-2}$ and $R^6$ have the abovementioned meaning, are deacylated on the amino group in the 5-position of the pyrazole ring, if appropriate in the presence of a diluent and if appropriate in the presence of a catalyst, or (g) the 5-amino-1-phenyl-pyrazole derivatives according to the invention, of the formula (Ig)

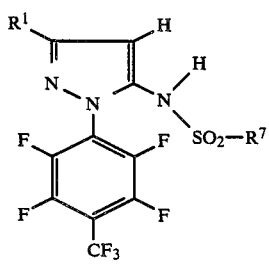
(Ig)

in which $R^1$ and $R^7$ have the abovementioned meaning, are obtained by a process in which 5-bis-sulphonyl-aminopyrazoles of the formula (Iv)

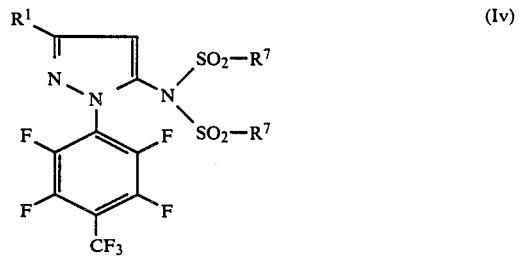
(Iv)

in which $R^1$ and $R^7$ have the abovementioned meaning, are split with bases, if appropriate in the presence of a diluent, or (h) the 5-amino-1-phenyl-pyrazole derivatives according to the invention, of the formula (Ih)

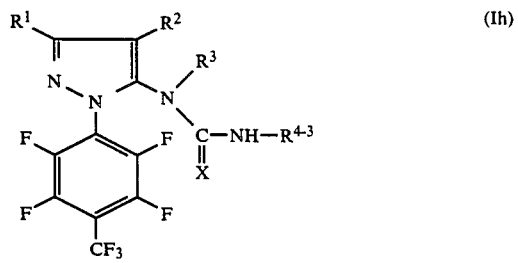
(Ih)

in which $R^{4-3}$ represents alkyl, or represents optionally substituted aryl and $R^1$, $R^2$, $R^3$ and X have the abovementioned meaning, are obtained by a process in which 5-amino-1-phenyl-pyrazoles of the formula (Is)

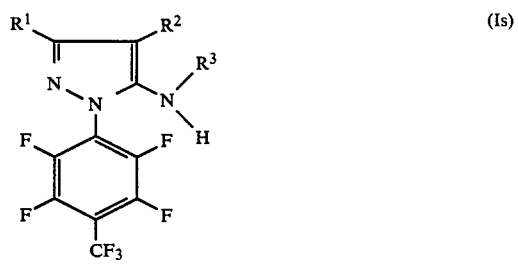
(Is)

in which $R^1$, $R^2$ and $R^3$ have the abovementioned meaning, are reacted with iso(thio)cyanates of the formula (VII)

$$R^{4-3}-N=C=X \qquad (VII)$$

in which $R^{4-3}$ and X have the abovementioned meaning, if appropriate in the presence of a diluent and if appropriate in the presence of an acid-binding agent, or (i) the 5-amino-1-phenyl-pyrazole derivatives according to the invention, of the formula (Ii)

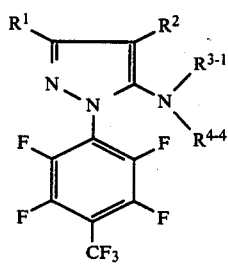 (Ii)

in which
R$^{4-4}$ represents alkyl,
R$^{3-1}$ represents hydrogen or alkyl and
R$^1$ and R$^2$ have the abovementioned meaning,
are obtained by a process in which 5-halogeno-pyrazoles of the formula (VIII)

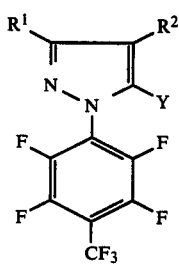 (VIII)

in which
Y represents halogen and
R$^1$ and R$^2$ have the abovementioned meaning,
are reacted with amines of the formula (IX)

 (IX)

in which
R$^{4-4}$ represents alkyl and
R$^{3-1}$ represents hydrogen or alkyl,
if appropriate in the presence of a diluent and if appropriate in the presence of an acid-binding agent, or (k) the 5-amino-1-phenyl-pyrazole derivatives according to the invention, of the formula (Ik)

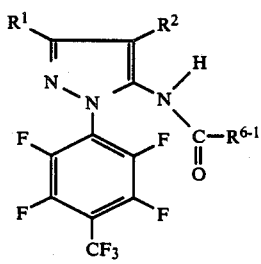 (Ik)

in which
R$^{6-1}$ represents alkoxy or alkylthio, or represents optionally substituted aryloxy, or represents optionally substituted arylthio, or represents alkylamino or dialkylamino, or represents optionally substituted arylamino and
R$^1$ and R$^2$ have the abovementioned meaning,
are obtained by a process in which (bis)carbamates of the formula (Iw)

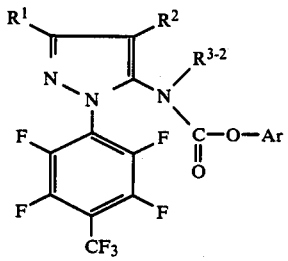 (Iw)

in which
R$^{3-2}$ represents hydrogen, or represents a radical $$-\overset{O}{\underset{\|}{C}}-O-Ar$$

wherein
Ar represents optionally substituted aryl and
R$^1$ and R$^2$ have the abovementioned meaning,
are reacted with compounds of the formula (X)

R$^{6-1}$—H     (X)

in which
R$^{6-1}$ has the abovementioned meaning,
if appropriate in the presence of a diluent and if appropriate in the presence of a basic catalyst, or (L) salts of 5-sulphonamido-pyrazole derivatives of the formula (Ix) according to the invention are obtained by a process in which 5-sulphonamido-pyrazoles of the formula (Ix)

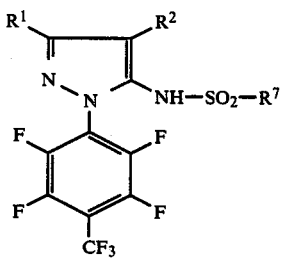 (Ix)

in which
R$^1$, R$^2$ and R$^7$ have the abovementioned meaning,
are reacted either with salts of the formula (XI)

M$^\oplus$—G$^\ominus$     (XI)

in which
M$^\oplus$ represents one equivalent of an inorganic or organic cation and
G$^\ominus$ represents one equivalent of a suitable counter-ion,
or with primary, secondary or tertiary amines, if appropriate in the presence of a diluent, or (m) salts of 5-perfluoroacylamido-pyrazole derivatives of the formula (Iy) according to the invention are obtained by a process in which 5-perfluoroacylamido-pyrazoles of the formula (Iy)

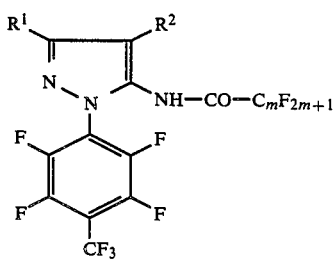

(Iy)

in which
R¹, R² and m have the abovementioned meaning,
are reacted either with salts of the formula (XI)

$$M^{\oplus}-G^{\ominus} \quad (XI)$$

in which
M⊕ and G⊖ have the abovementioned meaning, or with primary, secondary or tertiary amines, if appropriate in the presence of a diluent.

Finally, it has been found that the new 5-amino-1-phenyl-pyrazoles of the general formula (I) have herbicidal properties, and in particular also selectively herbicidal and plant growth-regulating properties.

Surprisingly, the 5-amino-1-phenyl-pyrazoles of the general formula (I) according to the invention also exhibit, in addition to a clearly improved general herbicidal activity against harmful plants, a considerably improved tolerance towards important crop plants in comparison with the 5-amino-1-aryl-pyrazoles known from the prior art, such as, for example, 4-nitro-5-propionamido-1-(2,3,5,6-tetrafluoro-4-trifluoromethyl-phenyl)-pyrazole, which are closely related compounds chemically and from the point of view of their action. Surprisingly, the 5-amino-1-phenyl-pyrazoles of the formula (I) according to the invention moreover also exhibit plant growth-regulating properties.

Formula (I) provides a general definition of the 5-amino-1-phenyl-pyrazoles according to the invention. Preferred compounds of the formula (I) are those in which
R¹ represents hydrogen, or represents straight-chain or branched alkyl with 1 to 8 carbon atoms,
R² represents hydrogen, nitro, nitroso, fluorine, chlorine, bromine or iodine, or represents a radical

wherein
R⁵ represents hydrogen, hydroxyl or straight-chain or branched alkyl with 1 to 8 carbon atoms, or represents in each case straight-chain or branched alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of the halogenoalkyl, with up to 9 identical or different halogen atoms, or furthermore represents cycloalkyl which has 3 to 7 carbon atoms and is optionally monosubstituted or polysubstituted by identical or different substituents from the group comprising halogen, C₁-C₄-alkyl and C₁-C₄-halogenoalkyl, or represents phenyl, phenoxy, phenylthio or phenylamino, in each case optionally monosubstituted or polysubstituted by identical or different substituents, possible substituents on the phenyl in each case being: halogen, in each case straight-chain or branched alkyl and alkoxy with in each case 1 to 4 carbon atoms and halogenoalkyl with 1 to 4 carbon atoms and 1 to 9 identical or different halogen atoms, R³ represents hydrogen, or represents a radical

or represents a radical —S(O)ₙ—R⁷ and
R⁴ represents hydrogen, or represents a radical

or represents a radical —S(O)ₙ—R⁷, or represents straight-chain or branched alkyl with 1 to 6 carbon atoms, or, in the case where R³ represents a radical —SO₂—R⁷ or a radical —CO—C_mF_{2m+1}, also represents one equivalent of an alkali metal cation, alkaline earth metal cation or transistor metal cation, bonded in salt form, or represents an ammonium ion, which is unsubstituted or mono- or polysubstituted by identical or different substituents from the group consisting of C₁-C₆-alkyl, phenyl and benzyl, wherein
R⁶ represents hydrogen, or represents straight-chain or branched alkyl with 1 to 12 carbon atoms, or represents in each case straight-chain or branched alkenyl or alkinyl with in each case 2 to 4 carbon atoms, or represents in each case straight-chain or branched alkoxyalkyl, alkylthioalkyl, alkoxy, alkylthio, alkylsulphonylalkyl, alkylsulphinylalkyl, alkylamino, dialkylamino or halogenoalkyl with in each case 1 to 4 carbon atoms in the individual alkyl parts and, in the case of the halogenoalkyl, with up to 9 identical or different halogen atoms, or furthermore represents cycloalkyl which has 3 to 7 carbon atoms and is optionally monosubstituted or polysubstituted by identical or different substituents from the group comprising halogen, C₁-C₄-alkyl and C₁-C₄-halogenoalkyl, or represents phenyl, phenoxy, phenylthio or phenylamino, in each case optionally monosubstituted or polysubstituted by identical or different substituents, possible substituents on the phenyl in each case being: halogen, in each case straight-chain or branched alkyl and alkoxy with in each case 1 to 4 carbon atoms and halogenoalkyl with 1 to 4 carbon atoms and 1 to 9 identical or different halogen atoms, R⁷ represents in each case straight-chain or branched alkyl or halogenoalkyl with in each case 1 to 4 carbon atoms and, if appropriate, 1 to 9 identical or different halogen atoms, or represents phenyl which is optionally monosubstituted or polysubstituted by identical or different substituents, possible substituents on the phenyl being: halogen, in each case straight-chain or branched alkyl and alkoxy with in each case 1 to 4 carbon atoms and halogenoalkyl with 1 to 4 carbon atoms and 1 to 9 identical or different halogen atoms, X represents oxygen or sulphur, n represents the number 0, 1 or 2 and
m represents the number 1, 2 or 3,
but wherein, in the case where $R^1$ and $R^3$ represent hydrogen and $R^2$ represents nitro, $R^4$ does not simultaneously represent a propionyl radical.

Particularly preferred compounds of the formula (I) are those in which
- $R^1$ represents hydrogen, methyl, ethyl, n- or i-propyl, or n-, i-, s- or t-butyl,
- $R^2$ represents hydrogen, nitro, nitroso, fluorine, chlorine, bromine or iodine, or represents a radical

wherein
- $R^5$ represents hydrogen, hydroxyl, methyl, ethyl, n- or i-propyl, n-, i-, s- or t-butyl, n- or i-pentyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 2-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents phenyl, phenoxy, phenylthio or phenylamino, in each case optionally mono-, di- or tri-substituted by identical or different substituents from the group comprising methyl, methoxy, chlorine and trifluoromethyl,
- $R^3$ represents hydrogen, or represents a radical

or represents a radical $-S(O)_n-R^7$ and
- $R^4$ represents hydrogen, or represents a radical

or represents a radical $-S(O)_n-R^7$, or represents methyl, ethyl, n- or i-propyl or n-, i-, s- or t-butyl, or, in the case where $R^3$ represents trifluoromethylcarbonyl, pentafluoroethylcarbonyl, heptafluoro-n-propylcarbonyl or heptafluoro-i-propylcarbonyl, or represents a radical $-SO_2-R^7$, also represents one equivalent of a sodium, potassium, magnesium, calcium, barium, copper, zinc, manganese, tin, iron, cobalt or nickel ion, bonded in salt form, or represents an ammonium ion which is optionally mono-, di- or trisubstituted by identical or different substituents from the group comprising methyl, ethyl, n- and i-propyl, n-, i-, s- and t-butyl and phenyl,
wherein
- $R^6$ represents hydrogen, methyl, ethyl, n- or i-propyl, n-, i-, s- or t-butyl, n- or i-pentyl, hexyl, heptyl, octyl, nonyl, decyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl or trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl,
- $R^7$ represents methyl, ethyl, n- or i-propyl, n-, i-, s- or t-butyl, chloromethyl, dichloromethyl, trichloromethyl or trifluoromethyl, or represents phenyl which is optionally mono-, di- or trisubstituted by identical or different substituents from the group comprising methyl, methoxy, chlorine and trifluoromethyl,
- X represents oxygen or sulphur and
- n represents the number 0, 1 or 2, but wherein, in the case where $R^1$ and $R^3$ represent hydrogen and $R^2$ represents nitro, $R^4$ does not simultaneously represent a propionyl radical.

A very particularly preferred group of compounds of the formula (I) are those in which
- $R^1$ represents hydrogen,
- $R^2$ represents hydrogen, nitro, nitroso, fluorine, chlorine, bromine or iodine, or represents a radical

wherein
- $R^5$ represents hydrogen, methyl, ethyl, n- or i-propyl, n-, i-, s- or t-butyl, n- or i-pentyl or represents phenyl, which is unsubstituted or mono-, di- or trisubstituted by identical or different substituents from the group comprising methyl, methoxy, chlorine and trifluoromethyl,
- $R^3$ represents hydrogen, or represents a radical

and
- $R^4$ represents hydrogen or represents a radical

or represents methyl, ethyl, n- or i-propyl or n-, i-, s- or t-butyl,
wherein
- $R^6$ represents hydrogen, methyl, ethyl, n- or i-propyl, n-, i-, s- or t-butyl, n- or i-pentyl, hexyl, heptyl, octyl, nonyl, decyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl or trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl, X represents oxygen or sulphur but wherein the following compound is excluded:

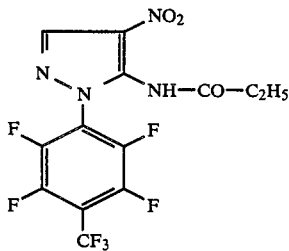

Another very particularly preferred group of compounds of the formula (I) are those in which $R^1$ represents hydrogen, $R^2$ represents hydrogen, nitro, nitroso, fluorine, chlorine, bromine or iodine, or represents a radical

wherein $R^5$ represents hydroxyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 2-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl and trifluoromethyl, or represents, phenoxy, phenylthio or phenylamino, in each case optionally mono-, di- or trisubstituted by identical or different substituents from the group comprising methyl, methoxy, chlorine and trifluoromethyl, $R^3$ represents hydrogen, or represents a radical

or represents a radical $-S(O)_n-R^7$ and $R^4$ represents hydrogen, or represents a radical

or represents a radical $-S(O)_n-R^7$, or represents methyl, ethyl, n- or i-propyl or n-, i-, s- or t-butyl, or, in the case where $R^3$ represents trifluoromethylcarbonyl, pentafluoroethylcarbonyl, heptafluoro-n-propylcarbonyl or heptafluoro-i-propylcarbonyl, or represents a radical $-SO_2-R^7$, also represents one equivalent of a sodium, potassium, magnesium, calcium, barium, copper, zinc, manganese, tin, iron, cobalt or nickel ion, bonded in salt form, or represents an ammonium ion which is optionally mono-, di- or trisubstituted by identical or different substituents from the group comprising methyl, ethyl, n- and i-propyl, n-, i-, s- and t-butyl and phenyl, wherein $R^6$ represents hydrogen, methyl, ethyl, n- or i-propyl, n-, i-, s- or t-butyl, n- or i-pentyl, hexyl, heptyl, octyl, nonyl, decyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group comprising fluorine, chlorine, bromine, methyl or trifluoromethyl, or represents phenyl, phenoxy, phenylthio or phenylamino, in each case optionally mono-, di- or trisubstituted by identical or different substituents from the group comprising methyl, methoxy, chlorine and trifluoromethyl, $R^7$ represents methyl, ethyl, n- or i-propyl, n-, i-, s- or t-butyl, chloromethyl, dichloromethyl, trichloromethyl or trifluoromethyl, or represents phenyl which is optionally mono-, di- or trisubstituted by identical or different substituents from the group comprising methyl, methoxy, chlorine and trifluoromethyl, X represents oxygen or sulphur and n represents the number 0, 1 or 2, but wherein, in the case where $R^1$ and $R^3$ represent hydrogen and $R^2$ represents nitro, $R^4$ does not simultaneously represent a propionyl radical. Very particularly preferred are also those compounds of the formula (I) in which $R^1$ represents methyl, ethyl, n- or i-propyl, n-, i-, s- or t-butyl and $R^2$, $R^3$ and $R^4$ have the particularly preferred meaning given above.

The following 5-amino-1-phenyl-pyrazoles of the general formula (I) may be mentioned specifically, in addition to the compounds mentioned in the preparation examples:

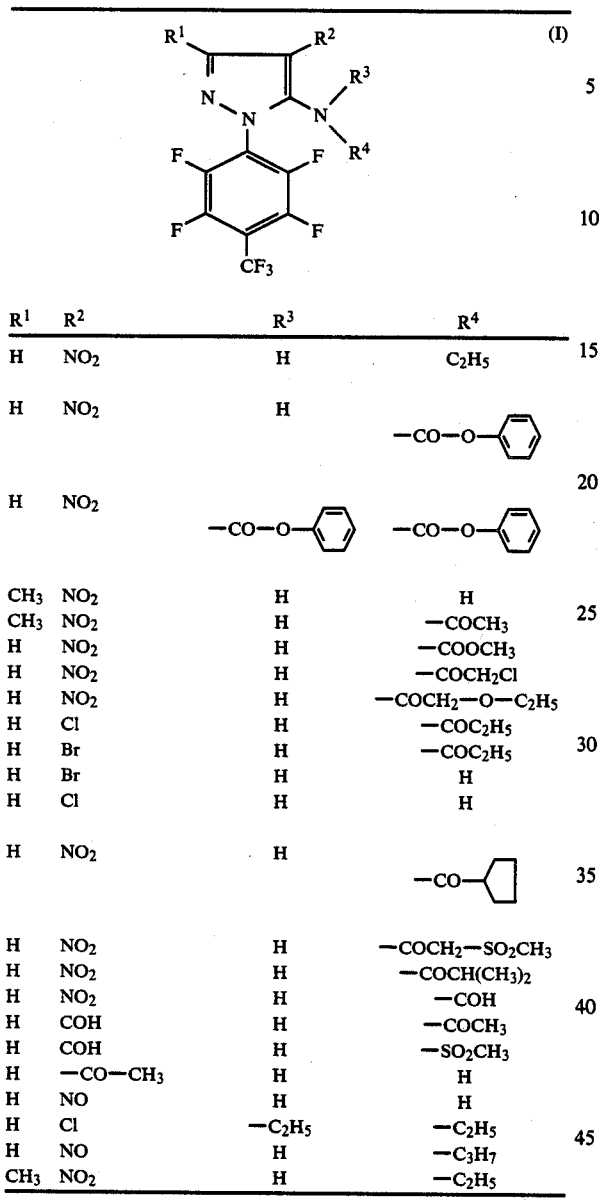

| R¹ | R² | R³ | R⁴ |
|---|---|---|---|
| H | NO₂ | H | C₂H₅ |
| H | NO₂ | H | —CO—O—C₆H₅ |
| H | NO₂ | —CO—O—C₆H₅ | —CO—O—C₆H₅ |
| CH₃ | NO₂ | H | H |
| CH₃ | NO₂ | H | —COCH₃ |
| H | NO₂ | H | —COOCH₃ |
| H | NO₂ | H | —COCH₂Cl |
| H | NO₂ | H | —COCH₂—O—C₂H₅ |
| H | Cl | H | —COC₂H₅ |
| H | Br | H | —COC₂H₅ |
| H | Br | H | H |
| H | Cl | H | H |
| H | NO₂ | H | —CO—C₅H₉ |
| H | NO₂ | H | —COCH₂—SO₂CH₃ |
| H | NO₂ | H | —COCH(CH₃)₂ |
| H | NO₂ | H | —COH |
| H | COH | H | —COCH₃ |
| H | COH | H | —SO₂CH₃ |
| H | —CO—CH₃ | H | H |
| H | NO | H | H |
| H | Cl | —C₂H₅ | —C₂H₅ |
| H | NO | H | —C₃H₇ |
| CH₃ | NO₂ | H | —C₂H₅ |

If, for example, 2,3,5,6-tetrafluoro-4-trifluoromethyl-phenyl-hydrazine and ethoxymethylenemalonic acid monoethyl ester-nitrile are used as starting substances, the course of the reaction in process (a) according to the invention can be represented by the following equation:

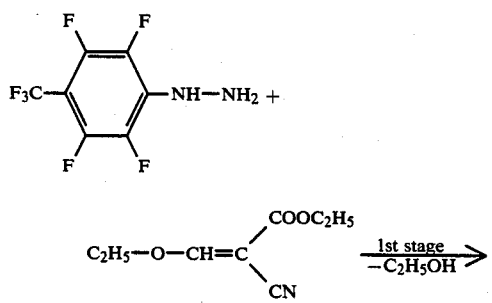

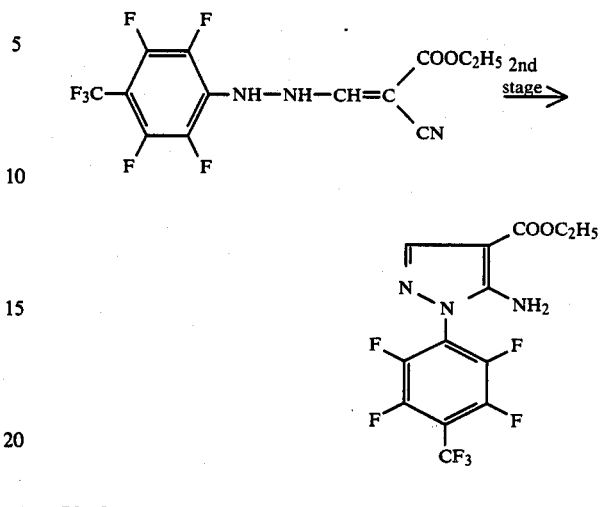

If, for example, 5-amino-1-(2,3,5,6-tetrafluoro-4-trifluoromethyl-phenyl)-4-ethoxycarbonyl-pyrazole is used as the starting substance, the course of the reaction in process (b) according to the invention can be represented by the following equation:

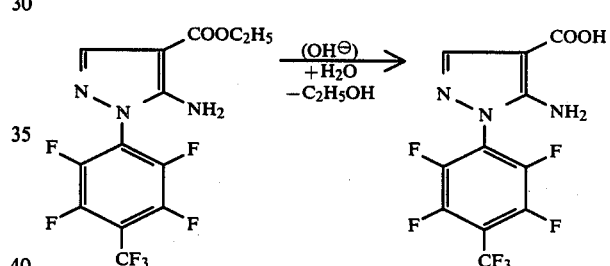

If, for example, 5-amino-1-(2,3,5,6-tetrafluoro-4-trifluoromethyl-phenyl)-pyrazole-4-carboxylic acid is used as the starting substance, the course of the reaction in process (c) according to the invention can be represented by the following equation:

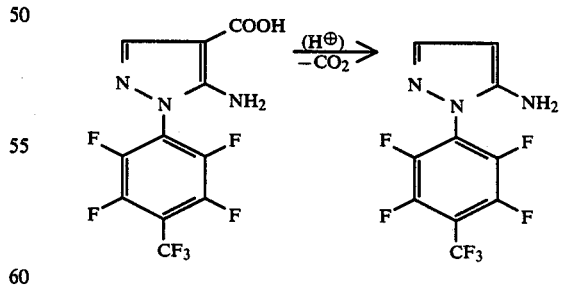

If, for example, 5-amino-1-(2,3,5,6-tetrafluoro-4-trifluoromethyl-phenyl)-pyrazole and propionyl chloride are used or methyl sulfonic acid chloride or methyliodide as starting substances, the course of the reaction in process (d-α), (d-β) and (d-μ) according to the invention can be represented by the following equation:

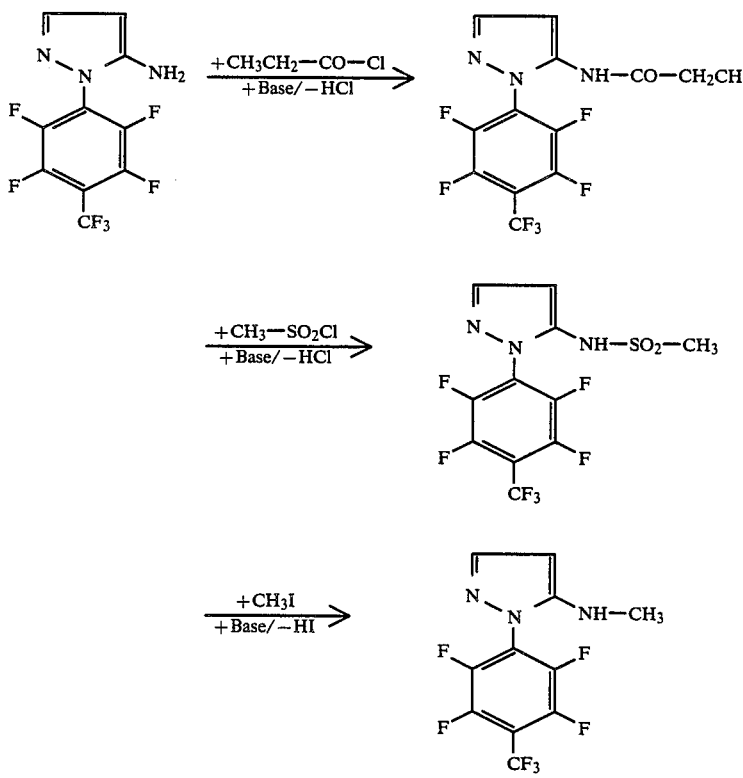

If, for example, 1-(2,3,5,6-tetrafluoro-4-trifluoromethyl-phenyl)-5-acetamido-pyrazole and nitric acid are used as starting substances, the course of the reaction in process (e) according to the invention can be represented by the following equation:

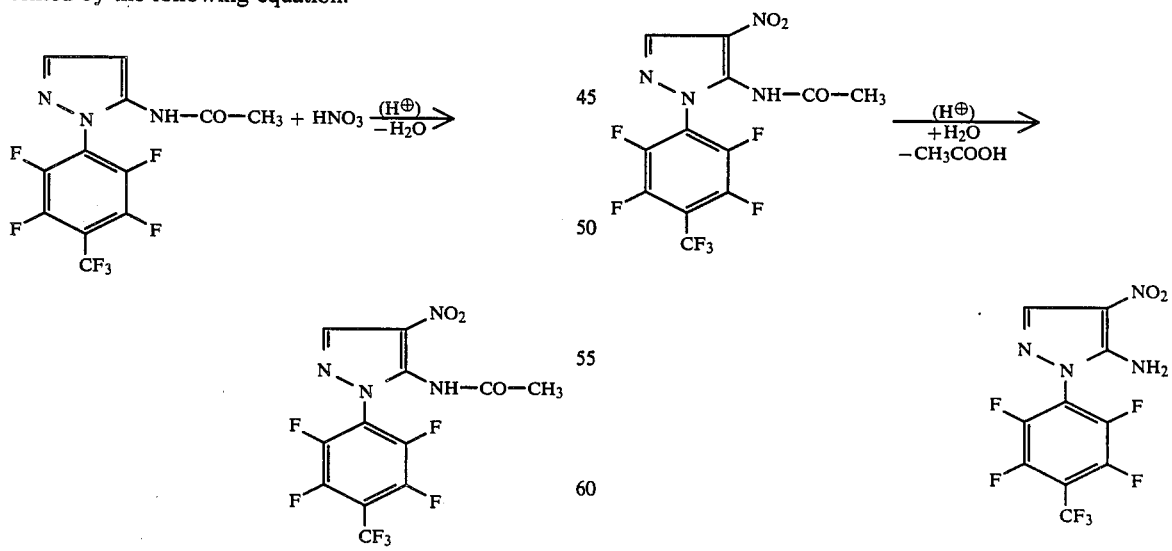

If, for example, 1-(2,3,5,6-tetrafluoro-4-trifluoromethyl-phenyl)-4-nitro-5-acetamido-pyrazole is used as the starting substance, the course of the reaction in process (f) according to the invention can be represented by the following equation:

If, for example, 5-[N,N-bis(methanesulphon)amido]-1-(2,3,5,6-tetrafluoro-4-trifluoromethyl-phenyl)-pyrazole and ammonia are used as starting substances, the course of the reaction in process (g) according to the invention can be represented by the following equation:

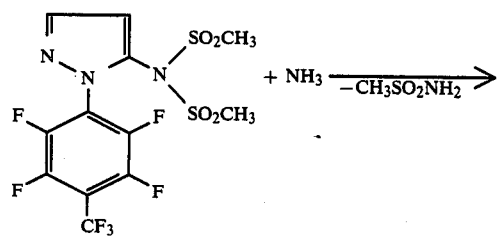 + NH$_3$ $\xrightarrow{-CH_3SO_2NH_2}$

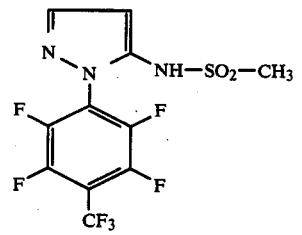

If, for example, 5-amino-1-(2,3,5,6-tetrafluoro-4-trifluoromethyl-phenyl)-pyrazole and methyl isocyanate are used as starting substances, the course of the reaction in process (h) according to the invention can be represented by the following equation:

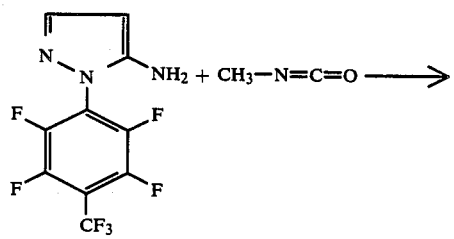 + CH$_3$—N=C=O ⟶

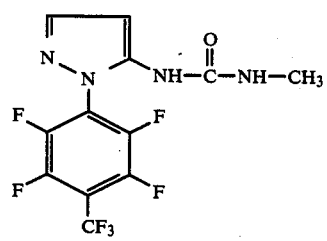

If, for example, 5-bromo-4-nitro-1-(2,3,5,6-tetrafluoro-4-trifluoromethyl-phenyl)-pyrazole and isopropylamine are used as starting substances, the course of the reaction in process (i) according to the invention can be represented by the following equation:

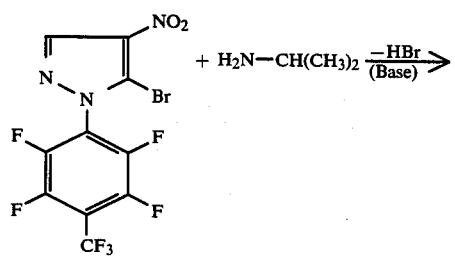 + H$_2$N—CH(CH$_3$)$_2$ $\xrightarrow[\text{(Base)}]{-HBr}$

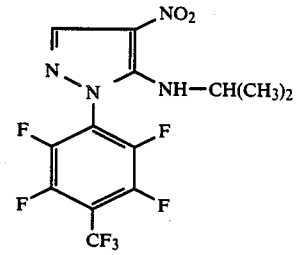

If, for example, 5-phenoxycarbonylamino-1-(2,3,5,6-tetrafluoro-4-trifluoromethyl-phenyl)-pyrazole and methanol are used as starting substances, process (k) according to the invention can be represented by the following equation:

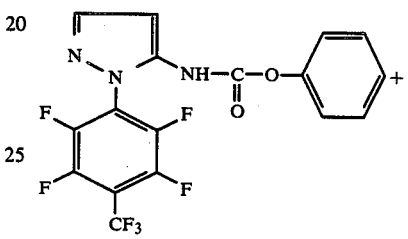 +

CH$_3$OH $\xrightarrow{-C_6H_5OH}$

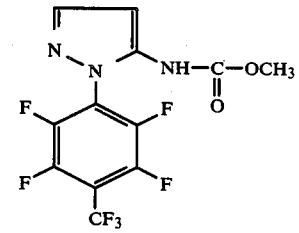

If, for example, 1-(2,3,5,6-tetrafluoro-4-trifluoromethyl-phenyl)-5-methanesulphonamido-pyrazole and isopropylamine are used as starting substances, the course of the reaction in process (L) according to the invention can be represented by the following equation:

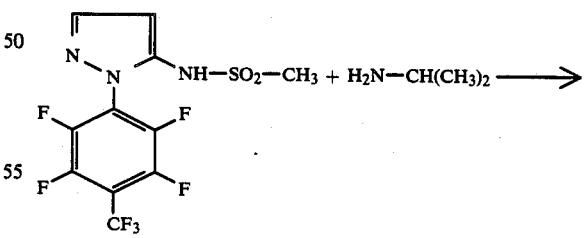

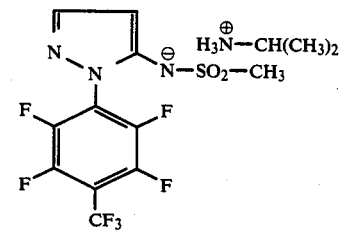

If, for example, 1-(2,3,5,6-tetrafluoro-4-trifluoromethyl-phenyl)-5-trifluoroacetamido-pyrazole and sodium bicarbonate are used as starting substances, the course of the reaction in process (m) according to the invention can be represented by the following equation:

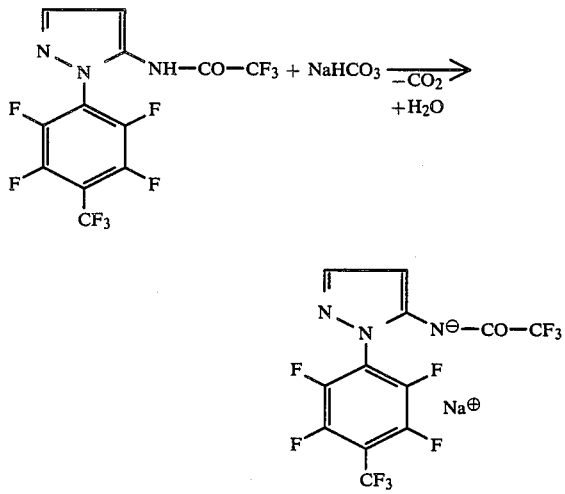

Formula (II) provides a definition of the 2,3,5,6-tetrafluoro-4-trifluoromethylphenylhydrazine which is required as the starting substance for carrying out process (a) according to the invention and is known (compare J. Chem. Soc. 1962, 1801, British UK Patent Application GB No. 2,123,420 and PCT International Application WO No. 82/331).

Formula (III) provides a general definition of the acrylonitrile derivatives furthermore required as starting substances for carrying out process (a) according to the invention. In this formula (III), $R^1$ and $R^2$ preferably represent those radicals which have already been mentioned as preferred for $R^1$ and $R^2$ in connection with the description of the substances of the formula (I) according to the invention. A preferably represents chlorine, bromine, hydroxyl, methoxy, ethoxy or dimethylamino.

The acrylonitrile derivatives of the formula (III) are known (compare DE-OS (German Published Specification) No. 3,129,429, DE-OS (German Published Specification) No. 3,206,878 and European Pat. No. 34,945; J. Chem. Soc. D. 1255; 1970, Can. J. Chem. 48, 2104–2109 (1970); J. Heterocyclic Chem. 19, 1267–1273 (1982); Can. J. Chem. 51, 1239–1244 (1973)), or they can be obtained by known processes in a simple analogous manner.

Formula (Ir) provides a general definition of the 4-alkoxycarbonyl-5-aminopyrazoles required as starting substances for carrying out process (b) according to the invention. In formula (Ir), $R^1$ preferably represents those radicals which have already been mentioned as preferred for this substituent in connection with the description of the substances of the formula (I) according to the invention. $R^8$ preferably represents straight-chain or branched alkyl with 1 to 4 carbon atoms, in particular methyl or ethyl.

The 4-alkoxycarbonyl-5-amino-pyrazoles of the formula (Ir) are compounds according to the invention and can be obtained with the aid of process (a) according to the invention.

Formula (Ib) provides a general definition of the 5-amino-1-phenyl-pyrazole derivatives required as starting substances for carrying out process (c) according to the invention. In this formula (Ib), $R^1$ preferably represents those radicals which have already been mentioned as preferred for this substituent in connection with the description of the substances of the formula (I) according to the invention.

The 5-amino-1-phenyl-pyrazole derivatives of the formula (Ib) are compounds according to the invention and can be obtained with the aid of process (b) according to the invention.

Formula (Is) provides a general definition of the 5-amino-1-phenyl-pyrazoles required as starting substances for carrying out process (d) according to the invention. In this formula (Is), $R^1$, $R^2$ and $R^3$ preferably represent those radicals which have already been mentioned as preferred for these substituents in connection with the description of the substances of the formula (I) according to the invention.

The 5-amino-1-phenyl-pyrazoles of the formula (Is) are compounds according to the invention.

5-Amino-1-phenyl-pyrazoles of the formula (Is) in which $R^3$ represents hydrogen can be obtained with the aid of processes (a), (b), (c), (e) or (f) according to the invention. 5-Amino-1-phenyl-pyrazoles of the formula (Is) in which $R^3$ is other than hydrogen can be obtained with the aid of processes (e), (f), (g) or (h) according to the invention.

5-Amino-1-phenyl-pyrazoles of the formula (Id) which can be prepared, for example, by process (d-α) according to the invention can also be employed as starting substances in process (d-α) according to the invention.

If the mono-alkylated, -acylated, -sulphenylated, -sulphinylated or -sulphonylated compounds obtained with the aid of processes (d-α), (d-β) or (d-γ) according to the invention are reacted again by one of these processes, the corresponding disubstituted compounds are obtained.

Formula (V), (Va) and (Vb) provides a general definition of the compounds furthermore required for carrying out process (d) according to the invention. In formulae (V), (Va) and (Vb), $R^{8-1}$ preferably represents straight-chain or branched alkyl with 1 to 6 carbon atoms, $R^6$, $R^7$, X and n preferably represent those radicals which have already been mentioned as preferred for these substituents in connection with the description of the substances of the formula (I) according to the invention, $A^1$ preferably represents chlorine or bromine, or represents a radical

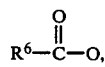

$A^2$ preferably represents chlorine or bromine and $A^3$ preferably represents chlorine, bromine, iodine, p-toluenesulphonyloxy or methoxysulphonyloxy.

The compounds of the formulae (V), (Va) and (Vb) are generally known compounds of organic chemistry.

Formula (It) provides a general definition of the 5-amino-1-phenyl-pyrazoles required as starting substances for carrying out process (e) according to the invention. In this formula (It), $R^1$, $R^3$ and $R^4$ preferably represent those radicals which have already been mentioned as preferred for these substituents in connection with the description of the substances of the formula (I) according to the invention.

The 5-amino-1-phenyl-pyrazoles of the formula (It) are compounds according to the invention and can be obtained with the aid of processes (a), (c), (d), (g), (i) or (k) according to the invention.

Formula (VI) provides a general definition of the electrophilic agents furthermore required as starting substances for carrying out process (e) according to the invention. In this formula (VI), $R^{2-1}$ preferably represents chlorine, bromine, nitroso or nitro, or represents formyl or alkanoyl with 1 to 6 carbon atoms in the alkyl part, or represents benzoyl which is optionally monosubstituted or polysubstituted by identical or different substituents, possible substituents being: halogen, in particular fluorine, chlorine or bromine, and in each case straight-chain or branched alkyl and alkoxy with in each case 1 to 4 carbon atoms, in particular methyl or methoxy, and halogenoalkyl with 1 to 4 carbon atoms and 1 to 9 identical or different halogen atoms, in particular trifluoromethyl.

$A^4$ preferably represents halogen, in particular chlorine or bromine, or represents hydroxyl, or represents alkyl- or arylsulphonyloxy, or represents alkanoyloxy or aroyloxy. Electrophilic reagents which can furthermore be used are sulphuryl chloride, phosphorus oxychloride/dimethylformamide, nitrating acid and other substances which can usually be employed for electrophilic replacement reactions.

The electrophilic agents of the formula (VI), like the other customary electrophilic reagents, are generally known compounds.

Formula (Iu) provides a general definition of the 5-acylamino-1-phenyl-pyrazoles required as starting substances for carrying out process (f) according to the invention.

In this formula (Iu), $R^1$ and $R^6$ preferably represent those radicals which have already been mentioned as preferred for these substituents in connection with the description of the substances of the formula (I) according to the invention.

$R^{2-2}$ preferably represents nitro, nitroso, fluorine, chlorine, bromine or iodine, and $R^{4-2}$ preferably represents hydrogen, or represents straight-chain or branched alkyl with 1 to 4 carbon atoms, in particular methyl or ethyl.

The 5-acylamino-1-phenyl-pyrazoles of the formula (Iu) are compounds according to the invention and can be obtained with the aid of processes (d) or (e) according to the invention.

Formula (Iv) provides a general definition of the 5-bis-sulphonyl-amino-pyrazoles required as starting substances for carrying out process (g) according to the invention. In this formula (Iv), $R^1$ and $R^7$ preferably represent those radicals which have already been mentioned as preferred for these substituents in connection with the description of the substances of the formula (I) according to the invention.

The 5-bis-sulphonyl-amino-pyrazoles of the formula (Iv) are compounds according to the invention and can be obtained with the aid of process (d) according to the invention.

Formula (Is) provides a general definition of the 5-amino-1-phenyl-pyrazoles required as starting substances for carrying out process (h) according to the invention.

In this formula (Is), $R^1$, $R^2$ and $R^3$ preferably have those meanings which have already been mentioned as preferred for these substituents in connection with the description of the substances of the formula (I) according to the invention.

The 5-amino-1-phenyl-pyrazoles of the formula (Is) are compounds according to the invention. Compounds of the formula (Is) in which $R^3$ represents hydrogen can be obtained with the aid of processes (a), (b), (c), (e) or (f) according to the invention.

Compounds of the formula (Is) in which $R^3$ is other than hydrogen can be obtained with the aid of processes (d), (e), (f), (g) or (h) according to the invention.

Formula (VII) provides a general definition of the iso(thio)cyanates furthermore required as starting substances for carrying out process (h) according to the invention. In this formula (VII), X represents oxygen or sulphur and $R^{4-3}$ preferably represents straight-chain or branched alkyl with 1 to 4 carbon atoms, or represents phenyl which is optionally mono-, di- or trisubstituted by identical or different substituents, possible substituents being: halogen and in each case straight-chain or branched alkyl and alkoxy with in each case 1 to 4 carbon atoms, or halogenoalkyl with 1 to 4 carbon atoms and 1 to 9 identical or different halogen atoms. $R^{4-3}$ particularly represents methyl or ethyl, or represent phenyl which is optionally mono-, di- or trisubstituted by identical or different substituents from the group comprising fluorine, chlorine, methyl, methoxy and trifluoromethyl.

The iso(thio)cyanates of the formula (VII) are generally known compounds of organic chemistry.

Formula (VIII) provides a general definition of the 5-halogenopyrazoles required as starting substances for carrying out process (i). In this formula (VIII), $R^1$ and $R^2$ preferably represent those radicals which have already been mentioned as preferred fo these substituents in connection with the description of the substances of the formula (I) according to the invention, and Y preferably represents chlorine or bromine.

5-halogeno-pyrazoles of the formula (VIII) are the subject of patent applications Ser. No. 816,643, filed Jan. 6, 1986, now pending, and Ser. No. 866,050, filed May 22, 1986, now pending.

They are obtained, for example, by a process in which alkoxymethylenemalonic acid esters of the formula (XII)

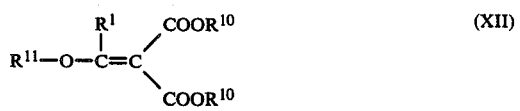

in which
$R^1$ has the abovementioned meaning and
$R^{10}$ and $R^{11}$ independently of one another each represent alkyl, in particular methyl or ethyl,
are first reacted with 2,3,5,6-tetrafluoro-4-trifluoromethylphenyl-hydrazines of the formula (II)

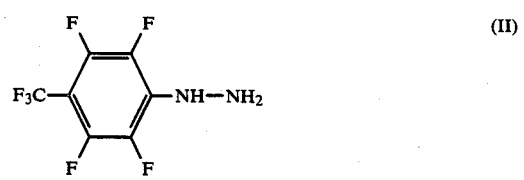

in a first stage, if appropriate in the presence of a diluent, such as, for example, methanol or ethanol, at temperatuers between +10° C. and +80° C., and the pyrazolecarboxylic acid esters thus obtainable, of the formula (XIII)

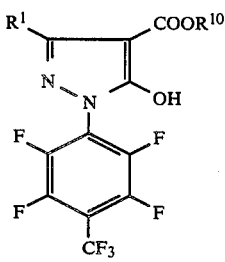

(XIII)

in which

R$^1$ and R$^{10}$ have the abovementioned meaning, are decarboxylated in a 2nd stage, if appropriate in the presence of a diluent, such as, for example, methanol, and if appropriate in the presence of a base, such as, for example, sodium hydroxide, at temperatures between +30° C. and +70° C., to give pyrazolinones of the formula (XIV)

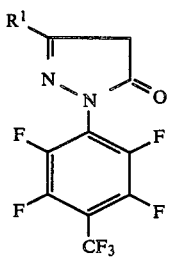

(XIV)

in which

R$^1$ has the abovementioned meaning, and these are reacted with halogenating agents, such as, for example, phosphorus oxychloride or phosphorus oxybromide, in a 3rd stage by generally customary processes (compare, for example, Ber. dtsch. chem. Ges. 28, 35 (1895) or Liebigs Ann. Chem. 373, 129 (1910)), and, if appropriate, the 5-halogeno-pyrazoles thus obtainable, of the formula (VIIIa)

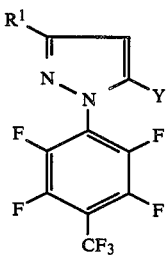

(VIIIa)

in which

R$^1$ and Y have the abovementioned meaning, are substituted in the 4-position with electrophilic agents of the formula (VI)

 (VI)

in which

R$^{2-1}$ represents halogen, nitroso, nitro, formyl, alkanoyl or aroyl and

A$^4$ represents an electron-withdrawing leaving group, or with other customary electrophilic reagents, in a 4th stage in the generally customary manner, if appropriate in the presence of a diluent, such as, for example, glacial acetic acid, and if appropriate in the presence of a catalyst or reaction auxiliary, such as, for example, acetic anhydride, in a procedure analogous to that of process (e) according to the invention.

If appropriate, the intermediate products of the formula (XIIa)

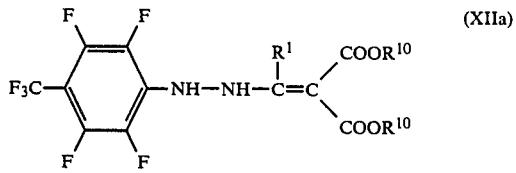

(XIIa)

in which

R$^1$ and R$^{10}$ have the abovementioned meaning, which occur in the reaction of alkoxymethylenemalonic acid esters of the formula (XII) with 2,3,5,6-tetrafluoro-4-trifluoromethylphenyl-hydrazine of the formula (II) can also be isolated and cyclized in a separate reaction stage.

If appropriate, the cyclization to give the pyrazolecarboxylic acid esters of the formula (XIII) and subsequent decarboxylation thereof can be carried out in one reaction stage as a "one-pot process" (compare, for example, Liebigs Ann. Chem. 373, 142 (1910)).

The alkoxymethylenemalonic acid esters of the formula (XII) are generally known compounds of organic chemistry.

Formula (IX) provides a general definition of the amines furthermore required as starting substances for carrying out process (i) according to the invention. In this formula (IX), R$^{4-4}$ preferably represents straight-chain or branched alkyl with 1 to 6 carbon atoms, in particular methyl, ethyl, n- or i-propyl or n-, i-, s- or t-butyl, and R$^{3-1}$ preferably represents hydrogen, or represents straight-chain or branched alkyl with 1 to 6 carbon atoms, in particular methyl, ethyl, n- or i-propyl or n-, i-, s- or t-butyl.

The amines of the formula (IX) are likewise generally known compounds of organic chemistry.

Formula (Iw) provides a general definition of the (bis)carbamates required as starting substances for carrying out process (k) according to the invention. In this formula (Iw), R$^1$ and R$^2$ preferably represent those radicals which have already been mentioned as preferred for these substituents in connection with the description of the substances of the formula (I) according to the invention, and R$^{3-2}$ represents a radical —CO—O—Ar or represents hydrogen, Ar preferably representing phenyl.

The (bis)carbamates of the formula (Iw) are compounds according to the invention and can be obtained with the aid of processes (d) or (e) according to the invention.

Formula (X) provides a general definition of the compounds furthermore required as starting substances for carrying out process (k) according to the invention. In this formula (X), R$^{6-1}$ preferably represent in each case straight-chain or branched alkoxy, alkylthio, alkylamino or dialkylamino with in each case 1 to 4 carbon atoms in the individual alkyl parts, or represents phenoxy, phenylthio or phenylamino, in each case monosubstituted or polysubstituted by identical or different substituents, possible substituents on the phenyl in each case being: halogen and in each case straight-chain or branched alkyl or alkoxy with in each case 1 to 4 carbon atoms, or halogenoalkyl with 1 to 4 carbon atoms and 1 to 9 identical or different halogen atoms, in particular methyl, methoxy, chlorine or trifluoromethyl, and $R^{6-1}$ particularly represents methoxy, ethoxy, methylthio, phenylthio or dimethylamino.

The compounds of the formula (X) are generally known compounds of organic chemistry.

Formula (Ix) provides a general definition of the 5-sulphonamido-pyrazoles required as starting substances for carrying out process (l) according to the invention. In this formula (Ix), $R^1$, $R^2$ and $R^7$ preferably represent those radicals which have already been mentioned as preferred for these substituents in connection with the description of the substances of the formula (I) according to the invention. The 5-sulphonamido-pyrazoles of the formula (Ix) are compounds according to the invention and can be obtained with the aid of processes (d), (e) and (g) according to the invention.

Formula (Iy) provides a general definition of the 5-perfluoroacylamido-pyrazoles required as starting substances for carrying out process (m) according to the invention. In this formula (Iy), $R^1$, $R^2$ and m preferably represent those radicals which have already been mentioned as preferred for these substituents in connection with the description of the substances of the formula (I) according to the invention.

The 5-perfluoroacylamido-pyrazoles of the formula (Iy) are compounds according to the invention and can be obtained with the aid of processes (d) and (e) according to the invention.

Formula (XI) provides a general definition of the salts furthermore required as starting substances for carrying out processes (l) and (m) according to the invention. Starting substances which are preferably used are alkali metal, alkaline earth metal, ammonium or transition metal hydroxides, oxides, carbonates, bicarbonates or readily soluble chlorides, sulphates, phosphates or nitrates, such as, for example, sodium, potassium or calcium hydroxide, carbonate or bicarbonate, calcium chloride, barium chloride, copper sulphate, nickel chloride or cobalt nitrate, or alkylamines, such as triethylamine, isopropylamine, diisopropylamine or butylamine.

The salts of the formula (XI) are generally known compounds.

Possible diluents for carrying out preparation process (a) are inert organic solvents both for the 1st and for the 2nd reaction stage. Solvents which are preferably used are alcohols, such as methanol, ethanol, propanol, butanol, ethylene glycol or ethylene glycol monomethyl or monoethyl ether.

Possible reaction auxiliaries for carrying out the 1st stage of preparation process (a) are organic or inorganic acids. Acids which are preferably used are sulphuric acid or acetic acid, if appropriate also in the presence of a buffer substance, such as, for example, sodium acetate.

The reaction temperatures can be varied within a certain range in carrying out the 1st stage of preparation process (a). The reaction is in general carried out between $-30°$ C. and $+50°$ C., preferably between $-20°$ C. and $+20°$ C.

Possible acid-binding agents for carrying out the 2nd stage of preparation process (a) are all the inorganic and organic bases which can usually be employed. Bases which are preferably used are alkali metal carbonates or bicarbonates, such as sodium carbonate, potassium carbonate or potassium bicarbonate.

Process (a) according to the invention can also be carried out directly in one reaction step, without isolation of the intermediate products of the formula (IV).

The reaction temperatures can be varied within a substantial range in carrying out the 2nd stage of preparation process (a), as in the single-stage reaction procedure. The reaction is in general carried out between $0°$ C. and $200°$ C., preferably between $+50°$ C. and $+150°$ C.

For carrying out preparation process (a), both in the one-stage and in the two-stage reaction procedure, in general 1.0 to 3.0 mols, preferably 1.0 to 1.5 mols, of acrylonitrile derivative of the formula (III), and in the case of the two-stage process, if appropriate 1.0 to 10.0 mols, of reaction auxiliary in the 1st stage and if appropriate 1.0 to 10.0 mols of acid-binding agent in the 2nd stage, are employed per mol of 2,3,5,6-tetrafluoro-4-trifluoromethylphenyl-hydrazine of the formula (II).

The reaction products of the formula (Ia) are worked up and isolated by customary processes, for example by removing the organic diluent, precipitating the reaction product in water and filtering off with suction and drying the product thus obtained.

Possible diluents for carrying out preparation process (b) are inorganic or organic solvents. Polar solvents are preferably used, in particular alcohols, such as, for example, methanol, ethanol or propanol, or mixtures thereof with water.

Possible catalysts for carrying out preparation process (b) are all the catalysts which can usually be employed for such ester hydrolysis reactions. Catalysts which are preferably used are bases, such as, for example, sodium hydroxide, sodium alcoholate or sodium carbonate, or acids, such as, for example, hydrochloric acid, hydrobromic acid or sulphuric acid.

The reaction temperatures can be varied within a substantial range in carrying out process (b) according to the invention. The reaction is in general carried out at temperatures between $20°$ C. and $150°$ C., preferably at temperatures between $50°$ C. and $100°$ C.

For carrying out preparation process (b), in general 1.0 to 15.0 mols, preferably 1.0 to 2.5 mols, of acidic or basic catalyst are employed per mol of 4-alkoxycarbonyl-5-amino-pyrazole of the formula (Ir) and the components are warmed to the required reaction temperature for several hours. The reaction products of the formula (Ib) are worked up, isolated and purified by customary processes.

Possible diluents for carrying out preparation process (c) are likewise inorganic or organic, preferably polar, solvent.

Alcohols, such as, for example methanol, ethanol or propanol, or mixtures thereof with water, are particularly suitable.

Possible catalysts for carrying out preparation process (c) are, preferably, acids, in particular inorganic mineral acids, such as hydrochloric acid, hydrobromic acid or sulphuric acid.

The reaction temperatures can be varied within a substantial range in carrying out preparation process (c). The reaction is in general carried out between $+50°$ C. and $+200°$ C., preferably between $+70°$ C. and $+130°$ C.

In carrying out process (c) according to the invention, in general 1.0 to 30.0 mols, preferably 1.0 to 15.0 mols, of catalyst acid are employed per mol of 5-amino-1-phenyl-pyrazole derivative of the formula (Ib) and the components are warmed at the required temperature for several hours. The reaction products of the formula (Ic) are worked up, isolated and purified by generally customary processes.

If an acid catalyst is used, it is also possible to carry out processes (b) (ester hydrolysis) and (c) (decarboxylation) according to the invention in one reaction step as a one-pot process. In this case also, the reaction is carried out and the reaction products are worked up and isolated by generally customary methods (compare also the preparation examples).

Possible diluents for carrying out process (d) according to the invention are inert organic solvents. Solvents which are preferably used are aliphatic, cyclic or aromatic, optionally halogenated hydrocarbons, such as, for example, benzine, benzene, toluene, xylene, pentane, hexane, heptane, cyclohexane, petroleum ether, ligroin, methylene chloride, chloroform, carbon tetrachloride, chlorobenzene or dichlorobenzene, ethers, such as diethyl ether, diisopropyl ether, dioxane, tetrahydrofuran or ethylene glycol diethyl ether or dimethyl ether, ketones, such as acetone, butanone, methyl isopropyl ketone or methyl isobutyl ketone, esters, such as ethyl acetate, nitriles, such as acetonitrile or propionitrile, or amides, such as dimethylformamide, dimethylacetamide, N-methylpyrrolidone or hexamethylphosphoric acid triamide. If compounds of the formulae (V), (Va) or (Vb) are used in liquid form, it is also possible to employ these in a corresponding excess as the diluent.

Possible acid-binding agents for carrying out process (d) according to the invention are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out preparation process (d). The reaction is in general carried out between −20° C. and +150° C., preferably between 0° C. and +100° C.

For carrying out preparation process (d), in general 1.0 to 20.0 mols, preferably 1.0 to 15.0 mols, of compound of the formula (V), (Va), or (Vb) and, if appropriate, 1.0 to 3.0 mols, preferably 1.0 to 2.0 mols, of acid-binding agent are employed per mol of 5-amino-1-phenylpyrazole of the formula (Is). The reaction is carried out and the reaction products of the formula (Id) are worked up and isolated in the generally customary manner.

Possible diluents for carrying out process (e) according to the invention are all the solvents which can usually be employed for such electrophilic substitutions. The acids or mixtures which are possible as reagents, such as, for example, sulphuric acid, nitric acid, sulphuryl chloride, phosphorus oxychloride/dimethylformamide or nitrating acid, are preferably used simultaneously as the diluent. If appropriate, inert organic solvents, such as, for example, glacial acetic acid or chlorinated hydrocarbons, such as methylene chloride, chloroform or carbon tetrachloride, can also be used as the diluent.

Possible catalysts or reaction auxiliaries for carrying out preparation process (e) are likewise the catalysts customary for such reactions; catalysts which are preferably used are acid catalysts, such as, for example, sulphuric acid, iron-III chloride or other Lewis acids or acetic anhydride.

The reaction temperatures can be varied within a substantial range in carrying out preparation process (e). The reaction is in general carried out between −50° C. and +200° C., preferably between −20° C. and +150° C.

For carrying out preparation process (e), in general 1.0 to 10.0 mols, preferably 1.0 to 5.0 mols, of electrophilic agent of the formula (VI) and, if appropriate, 0.1 to 10 mols of catalyst or reaction auxiliary are employed per mol of 5-amino-1-phenyl-pyrazole of the formula (It). The reaction is carried out and the reaction products of the formula (Ie) are worked up and isolated in the generally customary manner.

Possible diluents for carrying out process (f) according to the invention are inorganic or organic polar solvents. Solvents which are preferably use are alcohols, such as, for example, methanol, ethanol or propanol, or mixtures thereof with water.

Possible catalysts for carrying out preparation process (f) are, preferably, acids, in particular hydrochloric acid or sulphuric acid.

The reaction temperatures can be varied within a substantial range in carrying out preparation process (f). The reaction is in general carried out between +20° C. and +150° C., preferably between +50° C. and +120° C.

For carrying out preparation process (f), in general 1.0 to 20.0 mols, preferably 1.0 to 10.0 mols, of catalyst acid are employed per mol of 5-acylamino-1-phenyl-pyrazole of the formula (Iu) and the components are warmed at the required temperature for several hours. The reaction products of the formula (If) are worked up, isolated and purified by customary methods.

Possible diluents for carrying out process (g) according to the invention are polar organic solvents or mixtures thereof with water. Solvents which are preferably used are alcohols, such as methanol, ethanol or propanol, or mixtures thereof with water.

Possible basic reaction participants in carrying out process (g) according to the invention are all the customary inorganic or organic bases. Bases which are preferably used are amines or ammonia solutions or alkali metal carbonates or bicarbonates, such as sodium or potassium carbonate or sodium bicarbonate.

The reaction temperatures can be varied within a substantial range in carrying out process (g) according to the invention. The reaction is in general carried out between 0° C. and 80° C., preferably between 20° C. and 40° C.

For carrying out process (g) according to the invention, in general 1.0 to 30.0 mols, preferably 1.0 to 15.0 mols, of base are employed per mol of 5-bis-sulphonylamino-pyrazole of the formula (Iv).

The reaction mixture is stirred in a suitable diluent until the starting substance can no longer be detected by chromatography (30 minutes to 20 hours). The reaction products of the formula (Ig) are worked up by customary methods.

Possible diluents for carrying out process (h) according to the invention are inert organic solvents. The diluents mentioned for process (d) are preferably used. If the compounds of the formula (VII) are used in liquid form, it is also possible for these to be employed in a corresponding excess as the diluent.

Possible reaction auxiliaries for carrying out process (h) according to the invention are tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (h). The reaction is in general carried out between $-20°$ C. and $+150°$ C., preferably between $0°$ C. and $+100°$ C.

For carrying out preparation process (h), in general 1.0 to 20.0 mols, preferably 1.0 to 15.0 mols, of compound of the formula (VII) and, if appropriate, 1.0 to 3.0 mols, preferably 1.0 to 2.0 mols, of reaction auxiliary are employed per mol of 5-amino-1-phenyl-pyrazole of the formula (Is). The reaction is carried out and the reaction products of the formula (Ih) are worked up and isolated in the generally customary manner.

Possible diluents for carrying out process (i) according to the invention are inert organic solvents. These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform or carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, process (i) according to the invention can be carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

However, it is also possible for a corresponding excess of the amine of the formula (IX) employed as a reaction partner to be used simultaneously as the acid-binding agent.

The reaction temperatures can be varied within a substantial range in carrying out process (i) according to the invention. The reaction is in general carried out at temperatures between $-20°$ C. and $+200°$ C., preferably at temperatures between $0°$ C. and $+150°$ C.

For carrying out process (i) according to the invention, in general 1.0 to 10.0, preferably 1.0 to 5.0, of amine of the formula (IX) are employed per mol of 5-halogeno-pyrazole of the formula (VIII). The reaction is carried out and the reaction products of the formula (Ii) are worked up and isolated by generally customary processes.

Possible diluents for carrying out process (k) according to the invention are inert organic solvents. Solvents which are preferably used are aliphatic or aromatic, optionally halogenated hydrocarbons, such as benzine, benzene, toluene, xylene, pentane, hexane, heptane, cyclohexane, petroleum ether, ligroin, methylene chloride, ethylene chloride, chloroform, carbon tetrachloride, chlorobenzene or dichlorobenzene, ethers, such as diethyl ether, diisopropyl ether, ethylene glycol dimethyl ether, tetrahydrofuran or dioxane, ketones, such as acetone, butanone, methyl isopropyl ketone or methyl isobutyl ketone, esters, such as ethyl acetate, nitriles, such as acetonitrile or propionitrile, amides, such as dimethylformamide, dimethylacetamide, N-methylpyrrolidone or hexamethylphosphoric acid triamide, or alcohols, such as methanol, ethanol or isopropanol.

However, it is also possible for the compounds of the formula (X) used as reaction components to be employed as the diluent in a corresponding excess.

If appropriate, process (k) according to the invention can be carried out in the presence of a basic catalyst. Possible catalysts are all the customary inorganic or organic bases. The bases mentioned for process (i) are preferably used.

The reaction temperatures can likewise be varied within a substantial range in process (k) according to the invention. The reaction is in general carried out between $0°$ C. and $+200°$ C., preferably between $+20°$ C. and $+150°$ C.

For carrying out process (k) according to the invention, in general 1 to 20 moles, preferably 1 to 10 mols, of the compound of the formula (X) and, if appropriate, 0.1 to 2 mols, preferably 0.1 to 1 mol, of catalyst are employed per mol of (bis)carbamate of the formula (Iw) and the components are warmed at the required temperature for several hours. The reaction products of the formula (Ik) are worked up and isolated by customary processes.

Possible diluents for carrying out processes (l) and (m) according to the invention are polar organic solvents, water or aqueous mixtures. Solvents which are preferably used are alcohols, such as, for example, methanol, ethanol or propanol, mixtures thereof with water or pure water.

The reaction temperatures can likewise be varied within a substantial range in carrying out preparation processes (l) and (m). The reaction is in general carried out between $0°$ C. and $+80°$ C., preferably between $+20°$ C. and $+40°$ C.

For carrying out processes (l) and (m) according to the invention, in general 1.0 to 10 mols, preferably 1.0 to 5.0 mols, of salt of the formula (XI) or of amine are employed per mol of 5-amido-pyrazole of the formula (Ix) or (Iy).

To prepare the sodium, potassium or ammonium salts, a compound of the formula (Ix) or (Iy) is reacted with sodium hydroxide, potassium hydroxide or ammonium hydroxide or an amine, in aqueous solution or in an organic solvent, such as acetone, methanol, ethanol or dimethylformamide, and the salts are isolated by filtration or by evaporation of the solution, and, if appropriate, are purified by recrystallization.

The calcium, barium, magnesium, manganese, copper, nickel, tin, iron or cobalt salts are prepared from the sodium salts by treatment with a corresponding inorganic metal salt, for exammple calcium chloride, barium chloride, copper sulphate, nickel chloride or cobalt nitrate. The calcium salts can also be prepared by treatment of a compound of the formula (Ix) or (Iy) with calcium hydroxide.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perenial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating dicotyledon weeds in monocotyledon and dicotyledon crops, such as, for example, wheat or soya bean.

The precursors of the formula (VIII) also have a powerful herbicidal activity.

The active compounds according to the invention furthermore exhibit an action as leaf insecticides.

The active compounds according to the invention moreover engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2,-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans. Mixtures with: N,N-dimethyl-N'-(3-chloro-4-methylphenyl)-urea; N,N-dimethyl-N'-(4-isopropylphenyl)-urea; 2,4-dichlorophenoxyacetic acid; 2,4-dichlorophenoxypropionic acid; (2-methyl-4-chlorophenoxy)-acetic acid; (4-chloro-2-methyl-phenoxy)propionic acid; 2-benzyloxyethyl, trimethylsilylmethyl or 2,2-diethoxyethyl 2-[4-(3,5-dichloropyrid-2-yloxy)-phenoxy]-propionate; methyl 5-(2,4-dichlorophenoxy)-2-nitrobenzoate; 3,5-diiodo-4-hydroxybenzonitrile; 2-chloro-N-{[(4-methoxy-6-methyl-1,3,5-triazin-2-yl)-amino]-carbonyl}benzenesulphonamide, 4-ethylamino-2-t-butylamino-6-methylthio-s-triazine; N-methyl-2-(benzothiazol-2-yloxy)-acetamide; N-(1-ethylpropyl)-3,4-dimethyl-2,6-dinitroaniline; chloroacetic acid N-(methoxymethyl)-2,6-diethylanilide; 2-ethyl-6-methyl-N-(1-methyl-2-methoxyethyl)-chloroacetanilide; 2,6-dinitro-4-trifluoromethyl-N,N-dipropylaniline; ethyl 2-{4-[[3-chloro-5-(trifluoromethyl)-2-pyridinyl]oxy]-phenoxy}-propanate and other triazinones are also possible. Surprisingly, some mixtures also exhibit a synergistic action.

Mixtures with other known active compounds, such as fungicides, insecticides, acaricides, nematicides, bird repellents, plant nutrients and agents which improve soil structure, are also possible.

The active compounds can be used as such, in the form of their fomulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

When the compounds according to the invention are used as herbicides, the amount of active compound applied can vary within a substantial range. It depends essentially on the nature of the desired effect. In general, the amounts applied are between 0.01 and 50 kg of active compound per hectare of soil surface, preferably between 0.05 and 5 kg per ha.

The preparation and use of the active compounds according to the invention can be seen from the following examples.

When the compounds according to the invention are used as plant growth regulators, the amounts applied can likewise be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

PREPARATION EXAMPLES

Example 1

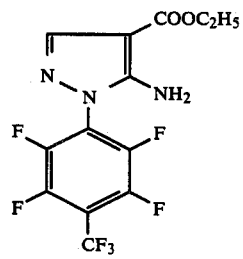

(Process a)

40 g (0.161 mol) of 2,3,5,6-tetrafluoro-4-trifluoromethylphenylhydrazine and 27.8 g (0.161 mol) of ethyl ethoxymethylenecyanoacetate are dissolved in 70 ml of ethanol and the solution is warmed under reflux for 10 hours. The solvent is distilled off in vacuo, the residue is suspended in 100 ml of diethyl ether, the suspension is filtered and the solid is dried. 52.2 g (87.4% of theory) of 5-amino-4-ethoxycarbonyl-1-(2,3,5,6-tetrafluoro-4-trifluoromethyl-phenyl)-pyrazole of melting point 175° C.–176° C. are obtained.

EXAMPLE 2

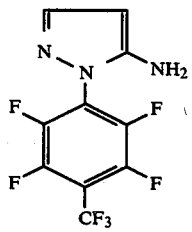

(Processes b+c)

100 g (0.270 mol) of 5-amino-4-ethoxycarbonyl-1-(2,3,5,6-tetrafluoro-4-trifluoromethyl-phenyl)-pyrazole are suspended in 250 ml of 50 percent strength aqueous sulphuric acid and the suspension is warmed to 120° C. in the course of 2 hours; the more highly volatile constituents are thereby distilled off over a bridge. The mixture is kept at 115° C.–120° C. for a further 3 hours and is cooled and diluted with 400 ml of water, the pH is brought to 2 with dilute aqueous sodium hydroxide solution and the precipitate formed is filtered off with suction. It is washed neutral with water and dried in vacuo. 77.3 g (96% of theory) of 5-amino-1-(2,3,5,6-tetrafluoro-4-trifluoromethyl-phenyl)-pyrazole of melting point 103° C.–104° C. are obtained.

EXAMPLE 3

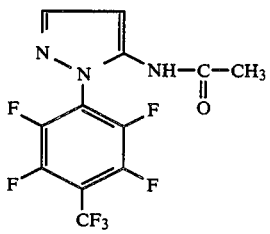

(Process d)

250 ml (0.26 mol) of acetic anhydride are added to 60 g (0.20 mol) of 5-amino-1-(2,3,5,6-tetrafluoro-4-trifluoromethyl-phenyl)-pyrazole in 170 ml glacial acetic acid, whereupon the reaction temperature rises from 20° C. to about 35° C. The mixture is stirred at room temperature for 16 hours and then poured onto 800 ml of water. The crystalline solid which has precipitated out is filtered off with suction, washed freely with water and acetic acid and dried in vacuo. 59.8 g (87.7% of theory) of 5-acetamido-1-(2,3,5,6-tetrafluoro-4-trifluoromethyl-phenyl)-pyrazole of melting point 102° C. –104° C. are obtained.

EXAMPLE 4

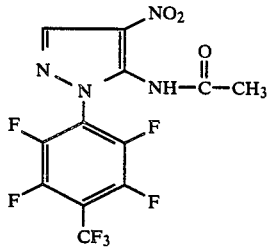

(Process e)

12.5 ml (0.13 mol) of acetic anhydride and 4.5 ml (0.105 mol) of 98 percent strength nitric acid are added in succession to 34.1 g (0.10 mol) of 5-acetamido-1-(2,3,5,6-tetrafluoro-4-trifluoromethyl-phenyl)-pyrazole in 85 ml of glacial acetic acid at about 15° C. The temperature is allowed to rise slowly to 25° C. and the mixture is subsequently stirred for 4 hours. The reaction solution is then poured onto 250 ml of water. The precipitate is filtered off, washed neutral and dried in vacuo. 36.3 g (94% of theory) of 5-acetamido-4-nitro-1-(2,3,5,6-tetrafluoro-4-trifluoromethyl-phenyl)-pyrazole of melting point 138° C.–140° C. are obtained.

EXAMPLE 5

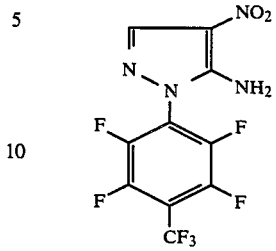

(Process f)

19.3 g (0.05 mol) of 5-acetamido-4-nitro-1-(2,3,5,6-tetrafluoro-4-trifluoromethyl-phenyl)-pyrazole are heated under reflux in a mixture of 40 ml of 37 percent strength hydrochloric acid and 70 ml of ethanol for 7 hours. The reaction mixture is freed from the ethanol in vacuo. 35 ml of water are added to the residue and the mixture is neutralized with dilute sodium hydroxide solution. The precipitate is filtered off with suction, washed with water and dried in vacuo. 15.7 g (91.4% of theory) of 5-amino-4-nitro-1-(2,3,5,6-tetrafluoro-4-trifluoromethyl-phenyl)-pyrazole of melting point 123° C.–126° C. are obtained.

EXAMPLE 6

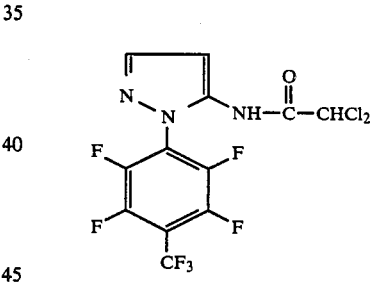

(Process d)

1.8 ml (0.022 mol) of anhydrous pyridine and 2.1 ml (0.021 mol) of 98 percent pure dichloroacetyl chloride are added in succession to a solution of 6 g (0.02 mol) of 5-amino-1-(2,3,5,6-tetrafluoro-4-trifluoromethyl-phenyl)-pyrazole in 35 ml of anhydrous acetonitrile. The temperature rises to 35° C. The mixture is subsequently stirred for four hours and then poured onto 150 ml of water. The oily precipitate is taken up in 50 ml of methylene chloride, the aqueous phase is separated off and the organic phase is washed with dilute hydrochloric acid, saturated sodium bicarbonate solution and saturated sodium chloride solution in succession, dried over magnesium sulphate and freed from the solvent in vacuo. 7.0 g (85% of theory) of 5-dichloroacetamido-1-(2,3,5,6-tetrafluoro-4-trifluoromethyl-phenyl)-pyrazole of melting point 112° C.–114° C. are obtained.

EXAMPLE 7

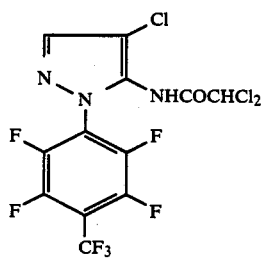

(Process e)

0.9 ml (0.011 mol) of sulphuryl chloride in 5 ml of methylene chloride are added dropwise to a solution of 4.1 g (0.01 mol) of 5-dichloroacetamido-1-(2,3,5,6-tetrafluoro-4-trifluoromethyl-phenyl)-pyrazole in 20 ml of methylene chloride at 0° C.–5° C. The mixture is stirred at room temperature for 16 hours and diluted with 30 ml of methylene chloride, the solution is washed with saturated sodium bicarbonate solution and sodium chloride solution in succession and dried over magnesium sulphate and the solvent is removed in vacuo. 3.9 g (87.2% of theory) of 4-chloro-5-dichloroacetamido-1-(2,3,5,6-tetrafluoro-4-trifluoromethyl-phenyl)-pyrazole of melting point 115° C.–116° C. are obtained.

EXAMPLE 8

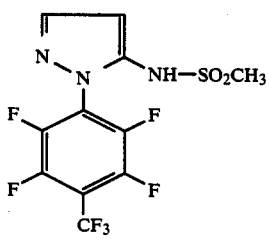

(Process g)

3.2 ml (0.041 mol) of 99 percent pure methanesulphonyl chloride are added to a solution of 6 g (0.02 mol) of 5-amino-1-(2,3,5,6-tetrafluoro-4-trifluoromethyl-phenyl)-pyrazole in 30 ml of anhydrous pyridine at 0° C. The mixture is stirred at room temperature for 16 hours and then poured onto about 400 ml of ice-water. 200 ml of methylene chloride are added, the organic phase is separated off and washed with dilute hydrochloric acid and the solvent is removed in vacuo. The residue is dissolved in 75 ml of ethanol, 15 ml of concentrated ammonia solution are added and the mixture is stirred at 0° C.–5° C. for 24 hours. The ethanol is removed in vacuo, the residue is extracted with methylene chloride and the organic phase is washed with dilute hydrochloric acid, saturated sodium bicarbonate solution and saturated sodium chloride solution in succession. After removal of the solvent in vacuo, 4.1 g (54.2% of theory) of 5-methanesulphonamido-1-(2,3,5,6-tetrafluoro-4-trifluoromethyl-phenyl)-pyrazole are obtained as a brown oil.

$^1$H-NMR(CDCl$_3$): $\delta=3.04$ s (3H, $\delta=6.48$ d (1H) and $\delta=7.82$ d (1H).

EXAMPLE 9

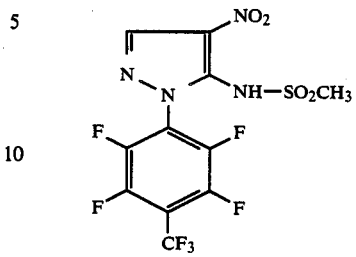

(Process e)

1.07 ml (0.011 mol) of acetic anhydride and 0.45 ml (0.0106 mol) of 98 percent strength nitric acid are added in succession to a solution of 3.8 g (0.01 mol) of 5-methanesulphonamido-1-(2,3,5,6-tetrafluoro-4-trifluoromethyl-phenyl)-pyrazole in 20 ml of glacial acetic acid at about 15° C. The mixture is stirred at room temperature for 16 hours and the reaction solution is poured onto 100 ml of water. The precipitate is filtered off with suction, washed neutral and dried in vacuo. 3.4 g (80% of theory) of 5-methanesulphonamido-4-nitro-1-(2,3,5,6-tetrafluoro-4-trifluoromethyl-phenyl)-pyrazole of melting point 163° C.–168° C. are obtained.

EXAMPLE 10

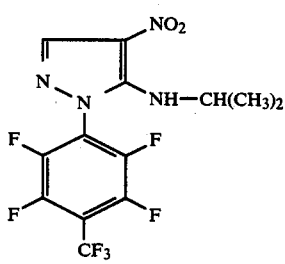

(Process i)

A mixture of 4.1 g (0.01 mol) of 1-(2,3,5,6-tetrafluoro-4-trifluoromethyl)-4-nitro-5-bromo-pyrazole and 7.8 g (0.13 mol) of isopropylamine in 100 ml of methylene chloride is stirred at room temperature for 50 hours. For working up, the reaction mixture is concentrated in vacuo, the residue is taken up in 40 ml of methylene chloride and the mixture is washed with 40 ml of water. The organic phase is dried over sodium sulphate and the solvent is distilled off in vacuo. The residue is made to crystallize by trituration with petroleum ether and is filtered off with suction and dried.

The 1-(2,3,5,6-tetrafluoro-4-trifluoromethyl)-4-nitro-5-isopropylamino-pyrazole (melting point 98°–100° C.) is separated off from the crude product by preparative HPLC. (High Pressure Liquid Chromatography)

PREPARATION OF THE STARTING SUBSTANCE

EXAMPLE VIII-1

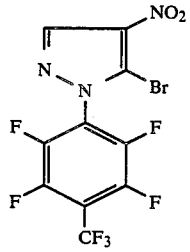

21.6 ml (0.18 mol) of t-butylnitrite are added dropwise to 20.6 g (0.06 mol) of 5-amino-4-nitro-1-(2,3,5,6-tetrafluoro-4-trifluoromethyl-phenyl)-pyrazole in 100 ml (1.125 mol) of bromoform in the course of 10 minutes, while stirring, whereupon the temperature of the reaction mixture rises to 50° C. When the addition has ended, the mixture is stirred at the reflux temperature for a further two hours and is concentrated in vacuo, the residue is taken up in methylene chloride, the mixture is washed several times with saturated sodium bicarbonate solution, 2n-hydrochloric acid and water and dried over sodium sulphate and the solvent is stripped off in vacuo. 22 g (89.9% of theory) of 5-bromo-4-nitro-1-(2,3,5,6-tetrafluoro-4-trifluoromethyl-phenyl)-pyrazole are obtained as a brown oil.

$^1$H-NMR(CDCl$_3$): δ=8.5 ppm.

MS (mass spectrum): M+ 407 and 409.

EXAMPLE 11

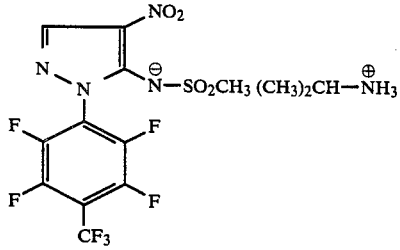

(Process 1)

1.5 ml (0.0175 mol) of anhydrous isopropylamine are added to a solution of 5 g (0.012 mol) of 5-methanesulphonamido-4-nitro-1-(2,3,5,6-tetrafluoro-4-trifluoromethyl-phenyl)-pyrazole in 60 ml of absolute ethanol. The mixture is stirred at room temperature for one hour, the solvent is removed in vacuo, the vitreous residue is dissolved in 50 ml of methylene chloride and the solution is concentrated in vacuo. 5 g (89% of theory) of the isopropylammonium salt of melting point 60° C.-63° C. are obtained.

The following 5-amino-1-phenyl-pyrazoles of the general formula (I) are obtained in a corresponding manner and in accordance with the general statements on the preparation:

| Example No. | R$^1$ | R$^2$ | $-N\begin{smallmatrix}R^3\\R^4\end{smallmatrix}$ | Melting point/°C. |
|---|---|---|---|---|
| 12 | H | H | —NH—C(O)—C$_2$H$_5$ | 115–117 |
| 13 | H | NO$_2$ | —NH—C(O)—CHCl$_2$ | 118–119 |
| 14 | H | H | NH—COCF$_3$ | 132–135 |
| 15 | H | H | —NH—COCHCl—CH$_3$ | 120–123 |
| 16 | H | H | —NHCOC$_3$H$_7$ | 56–59 |
| 17 | H | H | —NHCOC$_5$H$_{11}$ | 58–61 |
| 18 | H | H | —NHCOCH$_2$—OCH$_3$ | 109–113 |
| 19 | H | NO$_2$ | —NHCOCH$_2$—OCH$_3$ | 70–73 |
| 20 | H | H | —NHCO—CHF$_2$ | 158–160 |
| 21 | H | NO$_2$ | —NHCOCF$_3$ | 112–114 |
| 22 | H | NO$_2$ | —NHCOC$_3$H$_7$ | 98–99 |
| 23 | H | NO$_2$ | —NH—COC$_5$H$_{11}$ | 93–95 |
| 24 | H | NO$_2$ | —NH—COCHClCH$_3$ | 69–72 |
| 25 | | | [structure: pyrazole with NO$_2$, N$^{\ominus}$—CO—CF$_3$, (CH$_3$)$_2$CH—N$^{\oplus}$H$_3$] | 123–128 |
| 26 | H | H | —NH—CO—H | 50–58 |
| 27 | H | H | —NH—CO—CH$_2$Cl | 108–110 |
| 28 | H | NO$_2$ | —NH—CO—H | 160–163 |
| 29 | H | NO$_2$ | —NH—CO—CH$_2$Cl | 83–84 |
| 30 | H | H | —NH—CO—cyclopentyl | 101–103 |
| 31 | H | NO$_2$ | —NH—CO—OCH$_3$ | oil |
| 32 | H | NO$_2$ | —NH—CO—cyclopentyl | 95–97 |

USE EXAMPLES

The compound shown below was employed as the comparison substance in the following use examples:

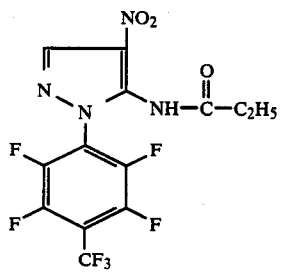

4-Nitro-5-propionamido-1-(2,3,5,6-tetrafluoro-4-trifluoromethyl-phenyl)-pyrazole (known from DE-OS (German Published Specification) No. 3,402,308)

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity and also crop plant selectivity compared with comparison substance (A) are shown, for example, by the compounds according to preparation Examples 1, 3, 5 and 24.

EXAMPLE B

Post-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is chosen so that the particular amounts of active compound desired are applied in 2,000 l of water/ha. After three weeks, the degree of damage to the plants is rated in % damage in comparison of the development of the untreated control. The figures denote:

0% = no action (like untreated control)
100% = total destruction

In this test, a clearly superior activity as well as crop plant selectivity compared with comparison substance (A) is shown, for example, by the compounds according to preparation Examples 1, 3, 5, 19 and 24.

EXAMPLE C

Defoliation and desiccation of the leaves of cotton

Solvent: 30 parts by weight of dimethylformamide
Emulsifier: 1 part by weight of polyoxyethylene sorbitan monolaurate.

To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. At this stage, the plants are sprayed with the preparations of active compound until dripping wet. After 1 week, the shedding of leaves and the desiccation of the leaves are rated, in comparison with the control plants.

In this test, a clear activity in comparison with the untreated control is shown, for example, by the compounds according to preparation Examples 2, 4, 7, 19, 21, 22, 23, 24, 28 and 29.

It is understood that the specification and examples are illustrative but not limitative of the present invention and that other embodiments within the spirit and scope of the invention will suggest themselves to those skilled in the art.

We claim:

1. A 5-amino-1-phenyl-pyrazole of the formula

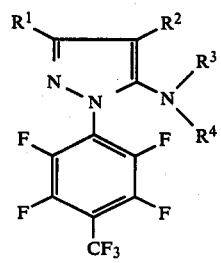

in which $R^1$ represents hydrogen, or represents straight-chain or branched alkyl with 1 to 8 carbon atoms, $R^2$ represents hydrogen, nitro, nitroso, fluorine, chlorine, bromine or iodine, or represents a radical

wherein $R^5$ represents hydrogen, hydroxyl or straight-chain or branched alkyl with 1 to 8 carbon atoms, or represents in each case straight-chain or branched alkenyl, alkinyl, alkoxyalkyl, alkylthioalkyl, alkoxy, alkylthio, alkylamino, dialkylamino or halogenoalkyl with in each case up to 4 carbon atoms in the individual alkyl parts and, in the case of the halogenoalkyl, with up to 9 identical or different halogen atoms, or furthermore represent cycloalkyl which has 3 to 7 carbon atoms and is optionally monosubstituted or polysubstituted by identical or different substituents from the group comprising halogen, $C_1$-$C_4$-alkyl and $C_1$-$C_4$-halogenoalkyl, or represents phenyl, phenoxy, phenylthio or phenylamino, in each case optionally substituted on the phenyl by halogen, alkyl, alkoxy or halogenoalkyl with in each case 1 to 4 carbon atoms and, if appropriate, up to 9 halogen atoms, $R^3$ represents hydrogen, or represents a radical

or represents a radical $—S(O)_n—R^7$ and $R^4$ represents hydrogen, or represents a radical

or represents a radical $—S(O)_n—R^7$, or represents straight-chain or branched alkyl with 1 to 6 carbon atoms, or, in the case where $R^3$ represents a radical $—SO_2—R^7$ or a radical $—CO—C_mF_{2m+1}$, also represents one equivalent of an alkali metal cation, alkaline earth metal cation or transition metal cation, bonded in salt form, or represents an ammonium ion, which is unsubstituted or mono- or polysubstituted by identical or different substituents from the group consisting of $C_1$-$C_6$-alkyl, phenyl and benzyl, wherein $R^6$ represents hydrogen, or represents straight-chain or branched alkyl with 1 to 12 carbon atoms, or represents in each case straight-chain or branched alkenyl or alkinyl with in each case 2 to 4 carbon atoms, or represents in each case straight-chain or branched alkoxyalkyl, alkylthioalkyl, alkoxy, alkylthio, alkylsulphonylalkyl, alkylsulphinylalkyl, alkylamino, dialkylamino or halogenoalkyl with in each case 1 to 4 carbon atoms in the individual alkyl parts and, in the case of the halogenoalkyl, with up to 9 identical or different halogen atoms, or furthermore represents cycloalkyl which has 3 to 7 carbon atoms and is optionally monosubstituted or polysubstituted by identical or different substituents from the group consisting of halogen, $C_1$-$C_4$-alkyl and $C_1$-$C_4$-halogenoalkyl, or represents phenyl, phenoxy, phenylthio or phenylamino, in each case optionally substituted on the phenyl by halogen, alkyl, alkoxy or halogenoalkyl with in each case 1 to 4 carbon atoms and, if appropriate, up to 9 halogen atoms, and X represents oxygen or sulphur, n represents the number 0, 1 or 2, m represents the number 1, 2 or 3 and $R^7$ represents in each case straight-chain or branched alkyl or halogenoalkyl with in each case 1 to 4 carbon atoms and, if appropriate, 1 to 9 identical or different halogen atoms, or represents phenyl which is optionally substituted by halogen, alkyl, alkoxy or halogenoalkyl with in each case 1 to 4 carbon atoms and, if appropriate, up to 9 identical or different halogen atoms, but wherein, in the case where $R^1$ and $R^3$ represents hydrogen and $R^2$ represents nitro, $R^4$ does not simultaneously represents a propionyl radical.

2. A 5-amino-1-phenyl-pyrazole according to claim 1, in which $R^1$ represents hydrogen, methyl, ethyl, n- or i-propyl or n-, i-, s- or t-butyl, $R^2$ represents hydrogen, nitro, nitroso, fluorine, chlorine, bromine or iodine, or represents a radical

wherein $R^5$ represents hydrogen, hydroxyl, methyl, ethyl, n- or i-propyl, n-, i-, s- or t-butyl, n- or i-pentyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 2-chloropropyl or heptafluoro-n-propyl, or represents cyclopropyl, cyclopentyl or cyclohexyl, in each case optionally mono-, di-, tri- or tetrasubstituted by identical or different substituents from the group consisting of fluorine, chlorine, bromine, methyl and trifluoromethyl, or represents phenyl, phenoxy, phenylthio or phenylamino, in each case optionally mono-, di- or trisubstituted by identical or different substituents from the group consisting of methyl, methoxy, chlorine and trifluoromethyl, $R^3$ represents hydrogen, or represents a radical

or represents a radical $—S(O)_n—R^7$ and $R^4$ represents hydrogen, or represents a radical

or represents a radical $—S(O)_n—R^7$, or represents methyl, ethyl, n- or i-propyl or n-, i-, s- or t-butyl, or, in the case where $R^3$ represents trifluoromethylcarbonyl, pentafluoroethylcarbonyl, heptafluoro-n-propylcarbonyl or heptafluoro-i-propylcarbonyl, or represents a radical $—SO_2—R^7$, also represents one equivalent of a sodium, potassium, magnesium, calcium, barium, copper, zinc, manganese, tin, iron, cobalt or nickel ion, bonded in salt form, or represents an ammonium ion which is optionally mono-, di- or trisubstituted by identical or different substituents from the group consisting of methyl, ethyl, n- and i-propyl, n-, i-, s- and t-butyl and phenyl, wherein $R^6$ represents hydrogen, methyl, ethyl, n- or i-propyl, n-, i-, s- or t-butyl, n- or i-pentyl, hexyl, heptyl, octyl, nonyl, decyl, undecyl, vinyl, allyl, propargyl, butenyl, methoxymethyl, ethoxymethyl, methoxyethyl, ethoxyethyl, methylthiomethyl, methoxy, ethoxy, methylsulphonylmethyl, methylsulphonylethyl, ethylsulphonylmethyl, ethylsulphonylethyl, methylsulphinylmethyl, methylsulphinylethyl, ethylsulphinylmethyl, ethylsulphinylethyl, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono-, di-, tri- or tetrasubstituted by identical or different substituents from the group consisting of fluorine, chlorine, bromine, methyl or trifluoromethyl, or represents phenyl, phenoxy, phenylthio or phenylamino, in each case optionally mono-, di- or trisubstituted by identical or different substituents from the group consisting of methyl, methoxy, chlorine and trifluoromethyl, and $R^7$ represents methyl, ethyl, n- or i-propyl, n-, i-, s- or t-butyl, chloromethyl, dichloromethyl, trichloromethyl or trifluoromethyl, or represents phenyl which is optionally mono-, di- or trisubstituted by identical or different substituents from the group consisting of methyl, methoxy, chlorine and trifluoromethyl.

3. A 5-amino-1-phenyl-pyrazole according to claim 1, in which $R^1$ represents hydrogen, $R^2$ represents hydrogen, nitro, nitroso, fluorine, chlorine, bromine or iodine, or represents a radical

wherein $R^5$ represents hydrogen, methyl, ethyl, n- or i-propyl, n-, i-, s- or t-butyl, n- or i-pentyl or represents phenyl which is unsubstituted or mono-, di- or trisubstituted by identical or different substituents from the group consisting of methyl, methoxy, chlorine and trifluoromethyl, $R^3$ represents hydrogen, or represents a radical

and $R^4$ represents hydrogen, or represents a radical

or represents methyl, ethyl, n- or i-propyl or n-, i-, s- or t-butyl, and $R^6$ represents hydrogen, methyl, ethyl, n- or i-propyl, n-, i-, s- or t-butyl, n- or i-pentyl, hexyl, heptyl, octyl, nonyl, decyl, undecyl, vinyl, allyl, propargyl, butenyl, methoxymethyl, ethoxymethyl, methoxyethyl, ethoxyethyl, methylthiomethyl, methoxy, ethoxy, methylthio, ethylthio, methylamino, ethylamino, dimethylamino, diethylamino, trifluoromethyl, trichloroethyl, dichlorofluoroethyl, difluorochloroethyl, chloromethyl, iodomethyl, bromomethyl, dichloromethyl, 1-chloroethyl, 2-chloroethyl, 2-bromoethyl, 3-chloropropyl or heptafluoro-n-propyl, or represents cyclopropyl, cyclopentyl or cyclohexyl, in each case optionally mono, di-, tri- or tetrasubstituted by identical or different substituents from the group consisting of fluorine, chlorine, bromine, methyl or trifluoromethyl, or represents phenyl, phenoxy, phenylthio or phenylamino, in each case optionally mono-, di- or trisubstituted by identical or different substituents from the group consisting of methyl, methoxy, chlorine and trifluoromethyl.

4. A compound according to claim 7, wherein such compound is 5-amino-4-ethoxycarbonyl-1-(2,3,5,6-tetrafluoro-4-trifluoromethyl-phenyl)-pyrazole of the formula

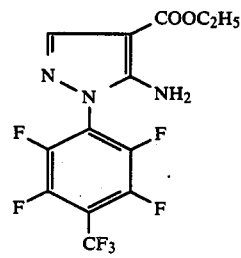

5. A compound according to claim 1, wherein such compound is 5-acetamido-1-(2,3,5,6-tetrafluoro-4-trifluoromethyl-phenyl)-pyrazole of the formula

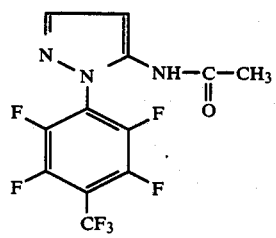

6. A compound according to claim 1, wherein such compound is 5-amino-4-nitro-1-(2,3,5,6-tetrafluoro-4-trifluoromethyl-phenyl)-pyrazole of the formula

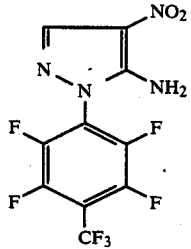

7. A compound according to claim 1, wherein such compound is 5-methoxyacetamido-4-nitro-1-(2,3,5,6-tetrafluoro-4-trifluoromethyl-phenyl)-pyrazole of the formula

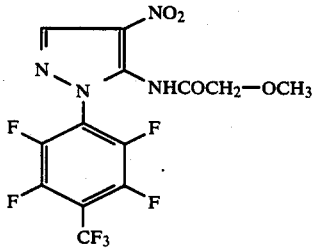

8. A compound according to claim 1, wherein such compound is 5-α-chloropropionamido-4-nitro-1-

(2,3,5,6-tetrafluoro-4-trifluoromethyl-phenyl)-pyrazole of the formula

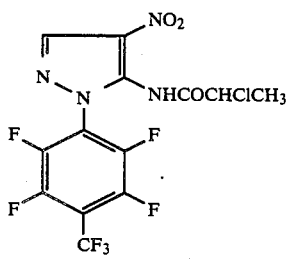

9. A compound according to claim 1, wherein such compound is 4-nitro-5-methyl-carbonylamino-1-(2,3,5,6-tetrafluoro-4-trifluoromethyl-phenyl)-pyrazole of the formula

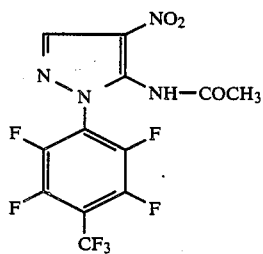

10. A 5-amino-1-phenyl-pyrazole selected from the group consisting of
    5-amino-4-ethoxycarbonyl-1-(2,3,5,6-tetrafluoro-4-trifluoromethyl-phenyl)-pyrazole,
    5-acetamido-1-(2,3,5,6-tetrafluoro-4-trifluoromethyl-phenyl)-pyrazole,
    5-amino-4-nitro-1-(2,3,5,6-tetrafluoro-4-trifluoromethyl-phenyl)-pyrazole,
    5-methoxyacetamido-4-nitro-1-(2,3,5,6-tetrafluoro-4-trifluoromethyl-phenyl)-pyrazole,
    5-α-chloropropionamido-4-nitro-1-(2,3,5,6-tetrafluoro-4-trifluoromethyl-phenyl)-pyrazole, and
    4-nitro-5-methyl-carbonylamino-1-(2,3,5,6-tetrafluoro-4-trifluoromethyl-phenyl)-pyrazole.

11. A herbicidal or plant growth-regulating composition comprising a herbicidal or plant growth regulating effective amount of a compound according to claim 1.

12. A method of combating unwanted vegetation which comprises applying to such vegetation or to a locus from which it is desired to exclude such vegetation a herbicidally effective amount of a compound according to claim 1.

13. The method according to claim 12, wherein such compound is
    5-amino-4-ethoxycarbonyl-1-(2,3,5,6-tetrafluoro-4-trifluoromethyl-phenyl)-pyrazole,
    5-acetamido-1-(2,3,5,6-tetrafluoro-4-trifluoromethyl-phenyl)-pyrazole,
    5-amino-4-nitro-1-(2,3,5,6-tetrafluoro-4-trifluoromethyl-phenyl)-pyrazole,
    5-methoxyacetamido-4-nitro-1-(2,3,5,6-tetrafluoro-4-trifluoromethyl-phenyl)-pyrazole or
    5-α-chloropropionamido-4-nitro-1-(2,3,5,6-tetrafluoro-4-trifluoromethyl-phenyl)-pyrazole.

14. A method or regulating the growth of plant which comprises applying to such plants or to a locus in which such plants are grown or to be grown a plant growth regulating effective amount of a compound according to claim 1.

15. The method according to claim 14, wherein such compound is
    5-amino-4-ethoxycarbonyl-1-(2,3,5,6-tetrafluoro-4-trifluoromethyl-phenyl)-pyrazole,
    5-acetamido-1-(2,3,5,6-tetrafluoro-4-trifluoromethyl-phenyl)-pyrazole,
    5-amino-4-nitro-1-(2,3,5,6-tetrafluoro-4-trifluoromethyl-phenyl)-pyrazole,
    5-methoxyacetamido-4-nitro-1-(2,3,5,6-tetrafluoro-4-trifluoromethyl-phenyl)-pyrazole or
    5-α-chloropropionamido-4-nitro-1-(2,3,5,6-tetrafluoro-4-trifluoromethyl-phenyl)-pyrazole.

* * * * *

UNITED STATES PATENT AND TRADEMARK OFFICE
CERTIFICATE OF CORRECTION

PATENT NO. : 4,787,930

DATED : November 29, 1988

INVENTOR(S) : Reinhold Gehring, et al

It is certified that error appears in the above-identified patent and that said Letters Patent is hereby corrected as shown below:

| | |
|---|---|
| Col. 7, line 28 | Delete "phenylpyrazoles" and substitute --phenyl-pyrazoles-- |
| Col. 12, line 25 | Delete "transistor" and substitute --transition-- |
| Col. 23, line 48 | After "(1982);" insert --and-- |
| Col. 27, line 1 | Delete "peratuers" and substitute --peratures-- |
| Col. 34, line 67 | Correct spelling of --example-- |
| Col. 35, line 30 | Correct --Cynodon-- |
| Col. 35, line 45 | Correct spelling of --perennial-- |
| Col. 50, line 4 | Delete "claim 7" and substitute --claim 1-- |
| Col. 46, line 66 | Delete "comprising" and substitute --consisting of-- |

Signed and Sealed this

Twenty-first Day of November, 1989

Attest:

JEFFREY M. SAMUELS

Attesting Officer  Acting Commissioner of Patents and Trademarks